US011116821B2

(12) United States Patent
Saal

(10) Patent No.: US 11,116,821 B2
(45) Date of Patent: Sep. 14, 2021

(54) METHODS FOR TREATING TRACHEOBRONCHOMALACIA

(71) Applicant: Alexion Pharmaceuticals, Inc., Boston, MA (US)

(72) Inventor: Howard M. Saal, Cincinnati, OH (US)

(73) Assignee: Alexion Pharmaceuticals, Inc., Boston, MA (US)

(*) Notice: Subject to any disclaimer, the term of this patent is extended or adjusted under 35 U.S.C. 154(b) by 176 days.

(21) Appl. No.: 16/325,910

(22) PCT Filed: Aug. 18, 2017

(86) PCT No.: PCT/US2017/047527
§ 371 (c)(1),
(2) Date: Feb. 15, 2019

(87) PCT Pub. No.: WO2018/035420
PCT Pub. Date: Feb. 22, 2018

(65) Prior Publication Data
US 2019/0209661 A1    Jul. 11, 2019

Related U.S. Application Data

(60) Provisional application No. 62/376,650, filed on Aug. 18, 2016.

(51) Int. Cl.
| A61K 38/46 | (2006.01) |
| A61P 19/00 | (2006.01) |
| A61K 9/00 | (2006.01) |
| C12N 15/52 | (2006.01) |
| A61K 38/16 | (2006.01) |
| C12N 9/16 | (2006.01) |
| C07K 19/00 | (2006.01) |

(52) U.S. Cl.
CPC ............ *A61K 38/46* (2013.01); *A61K 9/0014* (2013.01); *A61K 9/0019* (2013.01); *A61K 38/16* (2013.01); *A61P 19/00* (2018.01); *C07K 19/00* (2013.01); *C12N 9/16* (2013.01); *C12N 15/52* (2013.01); *C12Y 301/03001* (2013.01)

(58) Field of Classification Search
None
See application file for complete search history.

(56) References Cited

U.S. PATENT DOCUMENTS

| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |

(Continued)

FOREIGN PATENT DOCUMENTS

| EP | 0478797 B1 | 4/1995 |
| EP | 0769554 A2 | 4/1997 |

(Continued)

OTHER PUBLICATIONS

Strensiq Prescribing information (https://alexion.com/documents/strensiq_uspi) (Year: 2020).*
Official Action for Russian Patent Application No. 2017123540, dated Jul. 8, 2019 (15 pages).
Di Rocco et al., "Craniosynostosis and hypophosphatasia," Arch Pediatr. 24(5S2):5S89-5S92 (2017).
Official Action for Japanese Application No. 2017-539393, dated Sep. 17, 2019 (7 pages).
Whyte et al., "Natural history of perinatal and infantile hypophosphatasia: a retrospective study," J Pediatr. 209:116-124.e4 (2019) (13 pages).
Leung et al., "Outcome of perinatal hypophosphatasia in manitoba mennonites: a retrospective cohort analysis," JIMD Rep. 11:73-78 (2013).

(Continued)

*Primary Examiner* — David W Berke-Schlessel
(74) *Attorney, Agent, or Firm* — Clark & Elbing LLP

(57) ABSTRACT

The disclosure features methods for treating tracheobronchomalacia (TBM) in a patient having hypophosphatasia (HPP), such as an infant, by administering a soluble alkaline phosphatase (sALP) to the patient.

27 Claims, 3 Drawing Sheets

Specification includes a Sequence Listing.

(56) References Cited

U.S. PATENT DOCUMENTS

| | | |
|---|---|---|
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 2158319 | 3/2010 |
| EP | 1759001 B1 | 4/2011 |
| EP | 2158319 B1 | 12/2011 |
| JP | H08-70875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |

(56) References Cited

FOREIGN PATENT DOCUMENTS

| | | |
|---|---|---|
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/015011 A1 | 1/2009 |
| WO | WO-2009/023270 A2 | 2/2009 |
| WO | WO-2009/006732 A9 | 3/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Taketani et al., Chapter 9: Hypophosphatasia, Human Pathobiochemistry. T. Oohashi et al. (eds.), 91-100 (2019).

Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).

Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).

Mornet, "The tissue nonspecific alkaline phosphatase gene mutations database," <http://www.sesep.uvsq.fr/03_hypo_mutations.php>, accessed Oct. 9, 2019 (14 pages).

Hancarova et al., "Hypophosphatasia due to uniparental disomy," Bone. 81:765-766 (2015) (2 pages).

Carden et al., "Tracheomalacia and tracheobronchomalacia in children and adults: an in-depth review," Chest. 127(3):984-1005 (2005).

Murgu et al., "Tracheobronchomalacia and excessive dynamic airway collapse," Respirology. 11(4):388-406 (2006).

International Search Report and Written Opinion for International Patent Application No. PCT/US2017/047527, dated Nov. 6, 2017 (10 pages).

Milián et al., "Hypophosphatasia—pathophysiology and treatment," available in PMC Sep. 22, 2014, published in final edited form as: Actual Osteol. 8(3):164-182 (2012) (21 pages).

Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).

Ali et al., "Isolation and characterization of calcifying matrix vesicles from epiphyseal cartilage," Proc Natl Acad Sci USA. 67(3):1513-20 (1970).

Anderson et al., "Pyrophosphate stimulation of calcium uptake into cultured embryonic bones. Fine structure of matrix vesicles and their role in calcification," Dev Biol. 34:211-227 (1973).

(56) References Cited

OTHER PUBLICATIONS

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-37 (2005).
Beertsen et al., "Root development in mice lacking functional tissue non-specific alkaline phosphatase gene: Inhibition of acellular cementum formation," J Dent Res. 78(6):1221-1229 (1999) (10 pages).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-225 (1978).
Bonilla, "Pharmacokinetics of immunoglobulin administered via intravenous or subcutaneous routes," Immunol Allergy Clin N Am. 28:803-819 (2008).
Byers et al., "Effect of enzyme replacement therapy on bone formation in a feline model of mucopolysaccharidosis type VI," Bone. 21(5):425-431 (1997).
Cameron et al., "Minireview: Natriuretic peptides during development of the fetal heart and circulation," Endocrinology. 144(6):2191-2194 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for European Patent Application No. 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, "Investigation of the role of FcRn in the absorption, distribution, and elimination of monoclonal antibodies," Dissertation: State University of New York at Buffalo, 2007 (Abstract only) (2 pages).
Greenberg et al., "A homoallelic Gly$^{317}$ to Asp mutation in ALPL causes the perinatal (lethal) form of hypophosphatasia in Canadian Mennonites," Genomics. 17:215-217 (1993).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in Akp2$^{-/-}$ mice," J Bone Miner Res. 21(9):1377-1386 (2006).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Jansonius, "Structure, evolution and action of vitamin B$_6$-dependent enzymes," Curr Opin Struct Biol. 8:759-769 (1998).

Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & Peptide Drug Delivery—Third International Conference: Minimally invasive delivery methods, Sep. 22-23, Philadelphia, PA, USA," IDrugs. 6(11):1043-5 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Milián, *Mammalian Alkaline Phosphatases: From Biology to Applications in Medicine and Biotechnology*, Wiley-VCH Verlag GmbH & Co., Weinheim, Germany (2006) (324 pages).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516, <http://www.ncbi.nlm.nih.gov/protein/AAF64516>, retrieved Apr. 16, 2013 (2 pages).
NCBI Protein Database Accession No. AAC33858, <http://www.ncbi.nlm.nih.gov/protein/AAC33858>, retrieved Apr. 16, 2013 (1 pages).
NCBI Protein Database Accession No. AAH21289, <http://www.ncbi.nlm.nih.gov/protein/AAH21289>, retrieved Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).

(56) References Cited

OTHER PUBLICATIONS

NCBI Protein Database Accession No. Q9NOVO. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321:297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharm Res. 14(7): 911-6 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33:405-412 (1983).
Wang et al., "A mouse model for achondroplasia produced by targeting fibroblast growth factor receptor 3," Proc Natl Acad Sci USA. 96:4455-4460 (1999).
Wang et al., "Structure-based chemical modification strategy for enzyme replacement treatment of phenylketonuria," Mol Genet Metab. 86:134-140 (2005).
Weiss et al., "A missense mutation in the human liver/bone/kidney alkaline phosphatase gene causing a lethal form of hypophosphatasia," Proc Natl Acad Sci USA. 85:7666-7669 (1988).
Whyte et al., "Enzyme-replacement therapy in life-threatening hypophosphatasia," N Engl J Med. 366(10):904-13 (2012).
Whyte et al., "Markedly increased circulating pyridoxal-5'-phosphate levels in hypophosphatasia," J Clin Invest. 76:752-756 (1985).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 37(2):309-17 (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Bernardi, "Chromatography of proteins on hydroxyapatite," Methods Enzymol. 27:471-9 (1973).

Boskey et al., "Matrix vesicles promote mineralization in a gelatin gel," Calcif Tissue Int. 60(3):309-15 (1997).
Ciancaglini et al., "Contribution of matrix vesicles and alkaline phosphatase to ectopic bone formation," Braz J Med Biol Res. 39(5):603-10 (2006).
Crawley et al., "Enzyme replacement therapy in a feline model of Maroteaux-Lamy syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al., "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Milián et al., "Enzyme replacement therapy for murine hypophosphatasia," J Bone Miner Res. 23(6):777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically $^{32}$P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).

(56) References Cited

OTHER PUBLICATIONS

Weninger et al., "Biochemical and morphological effects of human hepatic alkaline phosphatase in a neonate with hypophosphatasia," Acta Paediatr Scand. Suppl. 360:154-160 (1989).

Whyte et al., "Infantile hypophosphatasia: enzyme replacement therapy by intravenous infusion of alkaline phosphatase-rich plasma from patients with Paget bone disease," J Pediatr. 101(3):379-86 (1982).

Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

Whyte, "Hypophosphatasia," in The Metabolic and Molecular Bases of Inherited Disease (8th ed.), pp. 5313-5329, 2001 (McGraw-Hill Book Company) (epub pp. 1-41).

Whyte, Chapter 18: Heritable Forms of Rickets and Osteomalacia. *Connective Tissue and Its Heritable Disorders*. Wiley-Liss, Inc., eds. R.M. Royce and B. Steinmann, 765-87 (2002).

Whyte et al., "Marrow cell transplantation for infantile hypophosphatasia," J Bone Miner Res. 18(4):624-36 (2003).

Yamamoto et al., "Prolonged survival and phenotypic correction of Akp2$^{-/-}$ hypophosphatasia mice by lentiviral gene therapy," J Bone Miner Res. 26(1):135-42 (2011).

Communication from Examining Division for European Application No. 05739065.0, dated Jun. 18, 2009 (6 pages).

Communication from Examining Division for European Application No. 05739065.0, dated Jun. 11, 2010 (5 pages).

Office Action for U.S. Appl. No. 12/793,517, dated Aug. 16, 2010 (9 pages).

Office Action for U.S. Appl. No. 13/071,445, dated Feb. 6, 2012 (12 pages).

Supplementary European Search Report for European Application No. 05739065, dated Dec. 2, 2008 (3 pages).

Choe et al., "Substrate profiling of cysteine proteases using a combinatorial peptide library identifies functionally unique specificities," J Biol Chem. 281(18):12824-12832 (2006).

Official Action for Japanese Application No. 2013-544989, dated Oct. 27, 2015 (3 pages).

Harris, "The human alkaline phosphatases: what we know and what we don't know," Clin Chim Acta. 186:133-50 (1989).

De la Croix Ndong et al., "Asfotase-alpha improves bone growth, mineralization and strength in mouse models of neurofibromatosis type-1," Nat Med. 20(8):904-10 (2014) (10 pages).

International Search Report and Written Opinion for International Patent Application No. PCT/US2016/047166, dated Nov. 7, 2016 (15 pages).

Ratner, "Alexion pays big for Synageva's rare disease drug candidate," Nat Biotechnol. 33(7):679 (2015).

Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).

Advisory Action for U.S. Appl. No. 11/484,870, dated Dec. 20, 2007 (4 pages).

Altarescu et al., "The efficacy of enzyme replacement therapy in patients with chronic neuronopathic Gaucher's disease," J Pediatr. 138(4):539-547 (2001).

Anderson et al., "Impaired calcification around matrix vesicles of growth plate and bone in alkaline phosphatase-deficient mice," Am J Pathol. 164(3):841-7 (2004).

Barranger et al., "Lessons learned from the development of enzyme therapy for Gaucher disease," J Inherit Metab Dis. 24(Suppl. 2):89-96 (2001).

Bobé et al., "Fas-mediated liver damage in MRL hemopoietic chimeras undergoing Ipr-mediated graft-versus-host disease," J Immunol. 159:4197-4204 (1997).

Boskey, "Amorphous calcium phosphate: the contention of bone," J Dent Res. 76:1433-1436 (1997).

Campbell et al., "Insulin-like growth factor (IGF)-binding protein-5-(201-218) region regulates hydroxyapatite and IGF-I binding," Am J Physiol Endocrinol Metab. 273:E1005-1013 (1997).

Cleland et al., "Emerging protein delivery methods," Curr Opin Biotechnol. 12:212-219 (2001).

Communication from Examining Division for European Application No. 08757088.3, dated Apr. 20, 2011 (4 pages).

Data Sheet for pFUSE-SEAP-hFC "Plasmid designed for the expression of a SEAP-Fc Fusion protein," Invivogen, San Diego, CA (4 pages) (1989).

Extended European Search Report for European Application No. 11774253.6, dated Oct. 14, 2013 (8 pages).

Extended European Search Report for European Application No. 11000196.3, dated Jun. 22, 2011 (6 pages).

Extended European Search Report for European Application No. 11004496.3, dated Aug. 26, 2011 (7 pages).

Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).

Fujisawa et al., "Acidic amino acid-rich sequences as binding sites of osteonectin to hydroxyapatite crystals," Biochim Biophys Acta. 1292:53-60 (1996).

Furbish et al., "Uptake and distribution of placental glucocerebrosidase in rat hepatic cells and effects of sequential deglycosylation," Biochim Biophys Acta. 673:425-434 (1981).

Hailing Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).

Hardy et al., "Dissection of a carboxy-terminal region of the yeast regulatory protein RAP1 with effects on both transcriptional activation and silencing," Mol Cell Biol. 12(3):1209-1217 (1992).

Hult et al., "Engineered enzymes for improved organic synthesis," Curr Opin Biotechnol. 14:395-400 (2003).

Hunter et al., "Modulation of crystal formation by bone phosphoproteins: structural specificity of the osteopontin-mediated inhibition of hydroxyapatite formation," Biochem J. 300:723-728 (1994).

Ikezawa, "Glycosylphosphatidylinositol (GPI)-anchored proteins," Biol Pharm Bull. 25(4):409-17 (2002).

International Search Report and Written Opinion for International Patent Application No. PCT/CA2005/000615, dated Aug. 18, 2005 (14 pages).

International Search Report and Written Opinion for International Patent Application No. PCT/CA2008/000923, dated Sep. 12, 2008 (11 pages).

International Search Report and Written Opinion for International Patent Application No. PCT/CA2011/050258, dated Jul. 29, 2011 (14 pages).

Kasugai et al., "Selective drug delivery system to bone: small peptide (Asp)$_6$ conjugation," J Bone Miner Res. 15(5):936-943 (2000).

Leone et al., "Allosteric modulation of pyrophosphatase activity of rat osseous plate alkaline phosphatase by magnesium ions," Int J Biochem Cell Biol. 30:89-97 (1998).

Meyer, "Can biological calcification occur in the presence of pyrophosphate?" Arch Biochem Biophys. 231(1):1-8 (1984).

Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).

Moss et al., "Association of inorganic-pyrophosphatase activity with human alkaline-phosphatase preparations," Biochem J. 102:53-57 (1967).

Murshed et al., "Unique coexpression in osteoblasts of broadly expressed genes accounts for the spatial restriction of ECM mineralization to bone," Genes Dev. 19:1093-1104 (2005).

(56) References Cited

OTHER PUBLICATIONS

Narisawa et al., "Abnormal vitamin B6 metabolism in alkaline phosphatase knock-out mice causes multiple abnormalities, but not the impaired bone mineralization,"J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).
Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated Jul. 16, 2013 (3 pages).
Patti et al., "Critical residues in the ligand-binding site of the *Staphylococcus aureus* collagen-binding adhesin (MSCRAMM)," J Biol Chem. 270(20):12005-11 (1995).
Reply to Final Office Action for U.S. Appl. No. 13/071,445, dated Oct. 25, 2012 (14 pages).
Reply to Final Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Supplementary European Search Report for European Application No. 08757088, dated Jun. 7, 2010 (5 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Chapter 70: Hypophosphatasia: Nature's window on alkaline phosphatase function in man," *Principles of Bone Biology, 2nd ed.*, Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Science. 290(5491):471-3 (2000).
Skolnick et al., "From genes to protein structure and function: novel applications of computational approaches in the genomic era," Trends Biotechnol. 18(1):34-9 (2000).
The Japanese Journal of Dermatology 115(6): 843-7 (2005).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Furuya et al., "Structural requirements of C-type natriuretic peptide for elevation of cyclic GMP in cultured vascular smooth muscle cells," Biochem Biophys Res Commun. 183(3):964-969 (1992).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol Cell Physiol. 270:C1311-18 (1996) (9 pages).

(56) References Cited

OTHER PUBLICATIONS

Horton et al., "Achondroplasia," Lancet. 370:162-72 (2007).
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Milián, "The Mammalian alkaline phosphatases: From Biology to Applications in Medicine and Biotechnology," Wiley-VCH Verlag, 107-185 (2006).
Miyazawa et al., "Cyclic GMP-dependent protein kinase II plays a critical role in C-type natriuretic peptide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31:101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274:2082-2086 (1996).
Potter et al., "Natriuretic peptides, their receptors, and cyclic guanosine monophosphate-dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223:1-6 (1996).
Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Whyte, Chapter 207: Hypophosphatasia. *The Online Metabolic and Molecular Bases for Inherited Disease*. McGraw-Hill Book Company, Valle et al. (eds.) (2001) (41 pages).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).

Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Chapter 4: Immunoglobulins: Structure and Function," *Microbiology and Immunology On-line*, University of South Carolina School of Medicine, <http://pathmicro.med.sc.edu/mayer/IgStruct2000.htm> (2009) (12 pages).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
Extended European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal pancraniosynostosis in a patient with infantile hypophosphatasia," Cleft Palate Craniofac J. 53(6):741-4, doi: 10.1597/15-027 (2016).
International Search Report and Written Opinion for International Patent Application No. PCT/US2015/058498, dated Jan. 22, 2016 (12 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Product Monograph, Including Patient Medication Information. Strensiq™ (asfotase alfa), Solution for Injection 40 mg/mL & 100 mg/mL," <http://alexionpharma.ca/documents/Strensiq-PM-asfotase-alfa-14Aug2015.aspx>, prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
Center for Drug Evaluation and Research, "Application No. 125513Orig1s000," <http://www.accessdata.fda.gov/drugsatfda_docs/nda/2015/125513Orig1s000MedR.pdf>, review completed Oct. 20, 2015; retrieved on Jun. 1, 2016 (254 pages).
International Search Report and Written Opinion for International Patent Application No. PCT/US2016/025721, dated Aug. 17, 2016 (18 pages).
Invitation to Pay Additional Fees for International Patent Application No. PCT/US2016/015366, dated Jun. 1, 2016 (7 pages).
Phillips et al., "A modified performance-oriented mobility assessment tool for assessing clinically relevant gait impairments and change in children with hypophosphatasia: development and vali-

(56) References Cited

OTHER PUBLICATIONS dation," 7th International Conference on Children's Bone Health, Jun. 27-30, Salzburg, Austria. Bone Abstracts. 4:P136 (2015) (2 pages).
Highlights of Prescribing Information for Strensig™ (asfotase alfa) Injection, Alexion Pharmaceuticals, Inc., <http://www.alexion.com/Documents/strensiq_pi-10-2015.aspx> (2015) (19 pages).
Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).
"View of NCT02235493 on Nov. 19, 2015," ClinicalTrials.gov archive, updated Nov. 19, 2015, retrieved Jan. 27, 2017 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).
International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, dated Oct. 9, 2015 (101 pages).
Reply Brief as Filed in U.S. Appl. No. 12/638,527, dated Apr. 22, 2016 (4 pages).
Examiner's Answer to Appeal Brief for U.S. Appl. No. 12/638,527, dated Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Milián et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, dated Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts,"J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)-->Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).

Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Wickramasinghe et al., "A case of hypophosphatasia," Ceylon Med J. 48(3):94-5 (2003).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, dated Aug. 10, 2017 (10 pages).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2016).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl-/- mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26): 1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).

(56) References Cited

OTHER PUBLICATIONS

Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 Å resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
European Collection of Authenticated Cell Cultures (ECACC), General Cell Collection: NS0, Catalogue No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).

(56) References Cited

OTHER PUBLICATIONS

Tenorio et al., "Molecular and clinical analysis of Alpl in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
De Roo et al., "Infantile hypophosphatasia without bone deformities presenting with severe pyridoxine-resistant seizures," Mol Genet Metab. 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of E. coli," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <http://abstracts.eurospe.org/hrp/0086/hrp0086FC2.5.htm> (2016) (4 pages).
International Search Report and Written Opinion for International Application No. PCT/US18/26868, dated Sep. 7, 2018 (30 pages).
International Preliminary Report on Patentability for International Patent Application No. PCT/US2016/049983, dated Sep. 11, 2018 (9 pages).
Sequence 4, U.S. Appl. No. 12/599,679, Retrieved Nov. 17, 2018 (2 pages).
Agochukwu et al., "Hearing loss in syndromic craniosynostoses: introduction and consideration of mechanisms," available in PMC Aug. 13, 2014, published in final edited form as: Am J Audiol. 23(2): 135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):525-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel mis-

(56) References Cited

OTHER PUBLICATIONS sense mutations (c.677T>C, p.M226T; c.1112C>T, p.T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1): 170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3 Suppl 3: S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).
Khanna et al., "Pictorial essay: The many faces of craniosynostosis," retrieved from <www.ncbi.nlm.nih.gov/pmc/articles/PMC3056371/> on Sep. 10, 2017, Indian J Radiol Imaging. 21(1):49-56 (2011) (8 pages).

Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Milián, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in ALPL, a common mutation resulting in the perinatal (lethal) form of hypophosphatasia

(56) References Cited

OTHER PUBLICATIONS in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology, vol. 1, Third Edition*. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices in: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Robert Koch Institute (2009) (136 pages).
Communication pursuant to Rule 164(2)(b) and Article 94(3) EPC for European Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).

\* cited by examiner

```
LVPEKEKDPK  YWRDQAQETL  KYALELQKLN  TNVAKNVIMF  LGDGMGVSTV  TAARILKGQL
HHNPGEETRL  EMDKFPFVAL  SKTYNTNAQV  PDSAGTATAY  LCGVKANEGT  VGVSAATERS
RCNTTQGNEV  TSILRWAKDA  GKSVGIVTTT  RVNHATPSAA  YAHSADRDWY  SDNEMPPEAL
SQGCKDIAYQ  LMHNIRDIDV  IMGGGRKYMY  PKNKTDVEYE  SDEKARGTRL  DGLDLVDTWK
SFKPRYKHSH  FIWNRTELLT  LDPHNVDYLL  GLFEPGDMQY  ELNRNNVTDP  SLSEMVVVAI
QILRKNPKGF  FLLVEGGRID  HGHHEGKAKQ  ALHEAVEMDR  AIGQAGSLTS  SEDTLTVVTA
DHSHVFTFGG  YTPRGNSIFG  LAPMLSDTDK  KPFTAILYGN  GPGYKVVGGE  RENVSMVDYA
HNNYQAQSAV  PLRHETHGGE  DVAVFSKGPM  AHLLHGVHEQ  NYVPHVMAYA  ACIGANLGHC
APASSLKDKT  HTCPPCPAPE  LLGGPSVFLF  PPKPKDTLMI  SRTPEVTCVV  VDVSHEDPEV
KFNWYVDGVE  VHNAKTKPRE  EQYNSTYRVV  SVLTVLHQDW  LNGKEYKCKV  SNKALPAPIE
KTISKAKGQP  REPQVYTLPP  SREEMTKNQV  SLTCLVKGFY  PSDIAVEWES  NGQPENNYKT
TPPVLDSDGS  FFLYSKLTVD  KSRWQQGNVF  SCSVMHEALH  NHYTQKSLSL  SPGKDIDDDD
DDDDDD    (SEQ ID NO: 1)
```

FIG. 1

METHODS FOR TREATING TRACHEOBRONCHOMALACIA

INCORPORATION OF SEQUENCE LISTING

The instant application contains a Sequence Listing, which has been submitted electronically in ASCII format and is hereby incorporated by reference in its entirety. The ASCII copy, created on Aug. 15, 2017, is named 50694-058WO2_Sequence_Listing_8.15.17_ST25.TXT and is 84 KB in size.

FIELD

The disclosure relates to methods for treating tracheobronchomalacia.

BACKGROUND

Hypophosphatasia (HPP) is a rare, heritable skeletal disease with an incidence of 1 per 100,000 births for the most severe forms of the disease. The disorder results from loss-of-function mutations in the gene encoding tissue-nonspecific alkaline phosphatase (TNSALP). HPP patients present a remarkable range of symptoms, from teeth loss or osteomalacia (rickets) to almost complete absence of bone mineralization in utero. Many patients with HPP present the characteristics of skeletal deformities, short stature, muscle and bone pain, impaired mobility, and premature loss of teeth. Perinatal-onset or infantile-onset HPP can also be characterized by the presence of rachitic chest deformity, vitamin B6-dependent seizures, and failure to thrive. In particular, HPP presenting at less than six months of age is often lethal due to respiratory insufficiency, with a low survival rate at one year of age.

Infants with HPP can exhibit respiratory compromise due to tracheobronchomalacia (TBM) and poorly mineralized ribs. TBM is a condition characterized by weakness of the tracheal and bronchial walls of the airway caused by hypotonia of myoelastic elements and softening of the supporting cartilage. The primary form of TBM is congenital. Severe TBM results in imminent risk of death from respiratory failure and complicated pulmonary infection. Thus, infants with TBM require aggressive therapy. In particular, HPP patients with TBM typically require assisted ventilation support to survive (Morrison, R J et al., Mitigation of tracheobronchomalacia with 3D-printed personalized medical devices in pediatric patients. Sci Transl Med.; 7(285): 285ra264 (2015)).

There exists a need for methods to treat tracheobronchomalacia in patients with HPP, such as infants with HPP.

SUMMARY

Disclosed are methods to treat tracheobronchomalacia (TBM) in a patient (e.g. a human) having hypophosphatasia (HPP) by administering a soluble alkaline phosphatase (sALP), such as asfotase alfa (e.g., SEQ ID NO: 1). In particular, the sALP can be effective for the treatment of TBM and symptoms thereof in patients having HPP, such as infants having perinatal-onset HPP, when administered in a dosage regimen that provides greater than or equal to 6 mg/kg/week of the sALP to the patient in need thereof. Exemplary dosage regimens can include, but are not limited to, about 3 mg/kg of the sALP administered three times a week, about 2.5 mg/kg of the sALP administered three times a week, about 1.3 mg/kg of the sALP administered six times a week, or about 5 mg/kg of the sALP administered three times a week. Additionally, the methods can include changing the dosage of and/or the frequency of administration of the sALP in order to determine the effective amount of the sALP to treat TBM and symptoms thereof in a patient having HPP. For instance, the dosage of an sALP can be increased to provide greater than or equal to 6 mg/kg/week, when the HPP patient does not exhibit an improvement in one or more symptoms of TBM after a treatment period of, e.g., at least two weeks, three weeks, one month, two months, three months, four months, five months, or six months.

A first aspect features a method of treating TBM in a patient having HPP (e.g., an infantile and perinatal-onset HPP patient) that includes administering an sALP to the patient in a dosage regimen that provides greater than or equal to 6 mg/kg/week of the sALP (e.g., asfotase alfa; SEQ ID NO: 1) to the patient. In particular, the sALP includes asfotase alfa (SEQ ID NO: 1) or an amino acid sequence having at least 95% sequence identity to the amino acid sequence of SEQ ID NO: 1. Administration of the sALP can result in an improvement in TBM in the patient, such as an improvement in TBM following administration of the sALP for a treatment period of, e.g., about one month, about two months, about three months, about four months, about five months, about six months, about seven months, about eight months, about nine months, about ten months, or longer.

For example, the sALP (e.g., SEQ ID NO: 1) can be administered twice a week, three times a week, four times a week, five times a week, six times a week, or seven times a week. In particular, the sALP can be administered on consecutive or alternating days. The dosage regimen can provide about 6.5 mg/kg/week to about 25 mg/kg/week of the sALP to the patient (e.g., the dosage regimen provides about 6.5 mg/kg/week of the sALP, about 7 mg/kg/week of the sALP, about 7.5 mg/kg/week of the sALP, about 7.8 mg/kg/week of the sALP, about 8 mg/kg/week of the sALP, about 8.5 mg/kg/week of the sALP, about 9 mg/kg/week of the sALP, about 10 mg/kg/week of the sALP, about 10.5 mg/kg/week of the sALP, about 11 mg/kg/week of the sALP, about 11.5 mg/kg/week of the sALP, about 12 mg/kg/week of the sALP, about 12.5 mg/kg/week of the sALP, about 13 mg/kg/week of the sALP, about 13.5 mg/kg/week of the sALP, about 14 mg/kg/week of the sALP, about 14.5 mg/kg/week of the sALP, about 15 mg/kg/week of the sALP, about 16 mg/kg/week of the sALP, about 17 mg/kg/week of the sALP, about 18 mg/kg/week of the sALP, about 19 mg/kg/week of the sALP, about 20 mg/kg/week of the sALP, about 21 mg/kg/week of the sALP, about 22 mg/kg/week of the sALP, about 23 mg/kg/week of the sALP, about 24 mg/kg/week of the sALP, or about 25 mg/kg/week of the sALP to the patient). In particular, the dosage regimen includes administering about 3 mg/kg of the sALP three times a week, about 2.5 mg/kg of the sALP three times a week, about 1.3 mg/kg of the sALP six times a week, or about 5 mg/kg of the sALP three times a week.

For instance, TBM in the patient having HPP can be characterized by one or more symptoms of TBM including, but not limited to, cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent dyspnea, continuous dyspnea, recurrent bronchitis, and recurrent pneumonia. The patient (e.g., an infantile and perinatal-onset HPP patient) can exhibit an improvement in one or more of the symptoms of TBM following administration of the sALP (e.g., SEQ ID NO: 1).

The method can further include increasing the dosage of the sALP (e.g., SEQ ID NO: 1) if the patient (e.g., an infantile and perinatal-onset HPP patient) does not exhibit an improvement in one or more of the symptoms of TBM following administration of the sALP for a treatment period of at least two weeks, three weeks, one month, two months, three months, four months, five months, or six months. For instance, the patient exhibits an improvement in one or more of the symptoms of TBM (e.g., cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent dyspnea, continuous dyspnea, recurrent bronchitis, and recurrent pneumonia) after receiving an increased dosage of the sALP. In particular, the patient exhibits an improvement in one or more of the symptoms of TBM after a treatment period of about one week, about two weeks, about three weeks, about one month, about two months, about three months, about four months, about five months, about six months, about seven months, about eight months, about nine months, about ten months, about eleven months, or about one year.

In the above aspect, the symptoms of TBM (e.g., cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent dyspnea, continuous dyspnea, recurrent bronchitis, and recurrent pneumonia) can be present in the patient (e.g., an infantile and perinatal-onset HPP patient) at birth or develop in the patient subsequent to birth. Additionally, the patient can be diagnosed with TBM prior to administration of the sALP (e.g., SEQ ID NO: 1).

The patient can require ventilator support prior to administration of the sALP (e.g., SEQ ID NO: 1). As a result of the methods, the patient (e.g., an infantile and perinatal-onset HPP patient) can exhibit decreased reliance on ventilator support, or no longer require ventilator support, after administration of the sALP. Moreover, the improvement in TBM can be sustained throughout administration of the sALP for a treatment period of at least one year, at least two years, at least three years, at least four years, at least five years, at least six years, at least seven years, at least eight years, at least nine years, at least ten years, or longer. In particular, the improvement in TBM can be relative to an untreated HPP patient (e.g. an infant) having TBM.

The method can further include, prior to or after administration of the sALP to the patient (e.g., an infantile and perinatal-onset HPP patient), performing a tracheostomy on the patient. Additionally, the method can include, prior to or after administration of the sALP to the patient, performing a bronchoscopy (e.g., flexible bronchoscopy and/or microlaryngobronchoscopy) on the patient.

In the above aspect, the patient (e.g., an infantile and perinatal-onset HPP patient) can require at least one of high frequency oscillatory ventilation, positive end-expiratory pressure (PEEP), continuous positive airway pressure (CPAP), bilevel or biphasic positive airway pressure (BiPAP), and intermittent positive pressure ventilation (IPPV), prior to and/or concurrently with administration of the sALP. In particular, the patient can require a PEEP of about 5 cm $H_2O$ to about 15 cm $H_2O$ (e.g., the PEEP is about 5 cm $H_2O$, about 6 cm $H_2O$, about 7 cm $H_2O$, about 8 cm $H_2O$, about 9 cm $H_2O$, about 10 cm $H_2O$, about 11 cm $H_2O$, about 12 cm $H_2O$, about 13 cm $H_2O$, about 14 cm $H_2O$, or about 15 cm $H_2O$). As a result of the methods, administration of the sALP can result in a decrease in the PEEP required by the patient, such as the PEEP required by the patient decreases by about 1 cm $H_2O$, about 2 cm $H_2O$, about 3 cm $H_2O$, about 4 cm $H_2O$, about 5 cm $H_2O$, about 6 cm $H_2O$, about 7 cm $H_2O$, about 8 cm $H_2O$, about 9 cm $H_2O$, or about 10 cm $H_2O$.

In the above aspect, the HPP patient can have at least one of perinatal-onset HPP and infantile-onset HPP. The HPP patient can be one that has not been previously administered the sALP (e.g., SEQ ID NO: 1). Additionally, administration of the sALP to the patient can occur about one month, about two months, about three months, about four months, about five months, or about six months after birth. In particular, the patient can be a human.

The patient (e.g., an infantile and perinatal-onset HPP patient) can exhibit one or more symptoms of HPP, which can include, but are not limited to, skeletal deformity, hypotonia, mobility impairments, bone deformity, joint pain, bone pain, muscle pain, bone fracture, muscle weakness, rickets, premature loss of deciduous teeth, incomplete bone mineralization, elevated blood and/or urine levels of phosphoethanolamine (PEA), elevated blood and/or urine levels of inorganic pyrophosphate (PPi), elevated blood and/or urine levels of pyridoxal 5'-phosphate (PLP), hypomineralization, rachitic ribs, hypercalciuria, short stature, waddling gait, HPP-related seizure, inadequate weight gain, craniosynostosis, and calcium pyrophosphate dihydrate crystal deposition. The one or more symptoms of HPP can be present in the patient at birth or develop in the patient subsequent to birth. As a result of the methods, the patient can exhibit an improvement in the one or more symptoms of HPP after administration of the sALP (e.g., SEQ ID NO: 1). Moreover, administration of the sALP can increase the survival of the patient.

The method can further include determining whether the patient (e.g., an infantile and perinatal-onset HPP patient) has a mutation in the patient's tissue non-specific alkaline phosphatase (TNALP) gene, in particular, the mutation in the TNALP gene is associated with HPP.

The sALP (e.g., SEQ ID NO: 1) can be administered to treat TBM and symptoms thereof in a patient having HPP (e.g., an infantile and perinatal-onset HPP patient) in a composition including a pharmaceutically acceptable excipient, carrier, or diluent, such as saline (e.g., sodium chloride and sodium phosphate). For example, the pharmaceutically acceptable excipient, carrier, or diluent includes 150 mM sodium chloride and 25 mM sodium phosphate. Moreover, the pharmaceutical composition can be administered to the patient parenterally (e.g., subcutaneously, intravenously, intramuscularly, intra-arterially, intrathecally, or intraperitoneally), enterally, or topically. In particular, the pharmaceutical composition can be administered to the patient subcutaneously.

In the above aspect, the sALP (e.g., SEQ ID NO: 1) is physiologically active toward PEA, PPi, and PLP, catalytically competent to improve skeletal mineralization in bone, and/or is the soluble extracellular domain of an alkaline phosphatase. For example, the sALP includes an amino acid sequence having at least 96%, 97%, 98%, or 99% sequence identity to the amino acid sequence of SEQ ID NO: 1, such as the sALP includes or consists of the amino acid sequence of SEQ ID NO: 1.

Additionally, the method can further include determining sALP activity in at least one of a serum sample and a blood sample from the patient (e.g., an infantile and perinatal-onset HPP patient). In particular, the sALP activity includes measuring at least one of PEA, PPi, and/or PLP in the serum and/or blood sample from the patient.

A second aspect features the use of an sALP including an amino acid sequence having at least 95% sequence identity (e.g., at least 96%, 97%, 98%, or 99% sequence identity) to the amino acid sequence of SEQ ID NO: 1 in the manufacture of a medicament for treating TBM in a patient (e.g., an infantile and perinatal-onset HPP patient) according to a dosage regimen. The dosage regimen provides greater than or equal to 6 mg/kg/week of the sALP (e.g., asfotase alfa; SEQ ID NO: 1) to the patient.

A third aspect features an sALP including an amino acid sequence having at least 95% sequence identity (e.g., at least 96%, 97%, 98%, or 99% sequence identity) to the amino acid sequence of SEQ ID NO: 1 for treating TBM in a patient having HPP (e.g., an infantile and perinatal-onset HPP patient). The sALP is administered to the patient in a dosage regimen that provides greater than or equal to 6 mg/kg/week of the sALP to the patient, in which the sALP (e.g., asfotase alfa; SEQ ID NO: 1) promotes an improvement in TBM in the patient.

Definitions

As used herein, "a" or "an" means "at least one" or "one or more" unless otherwise indicated. In addition, the singular forms "a," "an," and "the" include plural referents unless the context clearly dictates otherwise.

As used herein, "about" refers to an amount that is ±10% of the recited value and is preferably ±5% of the recited value, or more preferably ±2% of the recited value. For instance, the term "about" can be used to modify all dosages or ranges recited herein by ±10% of the recited values or range endpoints.

By "asfotase alfa" is meant a human TNSALP (hTNSALP) fusion protein formulated for the treatment of HPP. Asfotase alfa (STRENSIQ®, Alexion Pharmaceuticals, Inc.) is a fusion protein including a soluble glycoprotein of two identical polypeptide chains, in which each polypeptide chain includes amino acid residues 1-726 of SEQ ID NO: 1. The structure of each polypeptide chain includes the catalytic domain of hTNSALP, the human immunoglobulin Gi Fc domain, and a deca-aspartate peptide used as a bone targeting domain (the structure hTNSALP-Fc-Dio). The two polypeptide chains are covalently linked by two disulfide bonds. Asfotase alfa has been approved under the trade name STRENSIQ® in the United States, Europe, Japan, Canada, Israel, Australia, and Korea.

The term "bronchoscopy," as used herein, refers to a method performed to visualize the airways of a patient, such as a patient having HPP (e.g., an infant with HPP, such as an infant having perinatal-onset HPP) to diagnose or treat lung diseases or conditions, such as tracheobronchomalacia (TBM). Bronchoscopy involves the insertion of a device, referred to as a bronchoscope, into the airways, usually through the nose or mouth, or occasionally through a tracheostomy. The bronchoscope can be a flexible or rigid tube that is typically less than about 2.5 cm in width and less than about 65 cm in length.

The term "bone-targeting moiety," as used herein, refers to an amino acid sequence of between 1 and 50 amino acid residues (such as 1, 2, 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, or 50 amino acid residues) in length having an affinity to bone matrix, such that the bone-targeting moiety, singularly, has an in vivo binding affinity to bone matrix that is about $10^{-6}$ M to about $10^{-15}$ M (e.g., $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M). For example, the bone-targeting moiety can include a series of consecutive aspartate (D) and/or glutamate (E) residues of number "n," in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50.

The term "catalytically competent," as used herein, refers to an sALP that hydrolyzes the bone mineralization inhibitor inorganic pyrophosphate (PPi) to provide inorganic phosphate (Pi), thereby decreasing the extracellular concentrations of PPi. A catalytically competent sALP improves skeletal mineralization in bone by regulating the concentration of PPi.

The term "dosage regimen" refers to the administration of a determined quantity of an active agent (e.g., an sALP including an amino acid sequence having at least 95% sequence identity to the amino acid sequence of SEQ ID NO: 1, such as asfotase alfa) calculated to produce a desired therapeutic effect (e.g., treatment of TBM, such as a reduction in one or many symptoms of TBM) at a particular frequency. An sALP, such as asfotase alfa, can be administered in a dosage regimen in association with any suitable pharmaceutical excipient, carrier, or diluent. For example, an sALP can be administered at a dosage regimen of greater than or equal to about 6 mg/kg/week to the patient, such as about 6.5 mg/kg/week of the sALP, about 7 mg/kg/week of the sALP, about 7.5 mg/kg/week of the sALP, about 7.8 mg/kg/week of the sALP, about 8 mg/kg/week of the sALP, about 8.5 mg/kg/week of the sALP, about 9 mg/kg/week of the sALP, about 10 mg/kg/week of the sALP, about 10.5 mg/kg/week of the sALP, about 11 mg/kg/week of the sALP, about 11.5 mg/kg/week of the sALP, about 12 mg/kg/week of the sALP, about 12.5 mg/kg/week of the sALP, about 13 mg/kg/week of the sALP, about 13.5 mg/kg/week of the sALP, about 14 mg/kg/week of the sALP, about 14.5 mg/kg/week of the sALP, about 15 mg/kg/week of the sALP, about 16 mg/kg/week of the sALP, about 17 mg/kg/week of the sALP, about 18 mg/kg/week of the sALP, about 19 mg/kg/week of the sALP, about 20 mg/kg/week of the sALP, about 21 mg/kg/week of the sALP, about 22 mg/kg/week of the sALP, about 23 mg/kg/week of the sALP, about 24 mg/kg/week of the sALP, or about 25 mg/kg/week of the sALP to the patient. In particular, the sALP can be administered multiple times per week (e.g., twice a week, three times a week, four times a week, five times a week, six times a week, or seven times a week) in the dosage regimen, such as on consecutive or alternating days.

By "extracellular domain" is meant any functional extracellular portion of a native protein, e.g., alkaline phosphatase. In particular, an extracellular domain lacks a signal peptide.

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more, but less than the entire length of, a reference nucleic acid molecule or polypeptide. For example, a polypeptide fragment may contain 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues of the reference polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of an ALP (e.g., SEQ ID NOs: 2-6), and may include additional C-terminal and/or N-terminal portions. Biological activity of such fragments can be tested in standard assays known in the art, e.g., by a non-compartmental analysis (NCA) to calculate pharmacokinetic parameters of the sALP fragment.

The terms "hypophosphatasia" and "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNSALP). HPP can be further characterized as, e.g., infantile HPP or perinatal HPP (e.g., benign perinatal HPP or lethal perinatal HPP). For instance, "infantile HPP" describes a patient having HPP that is about three years of age or younger, whereas "perinatal HPP" describes a patient having HPP immediately before or after birth (e.g., one to four weeks after birth). The age of onset of HPP, such as when the subject exhibits symptoms of HPP, can also be categorized as, e.g., perinatal-onset HPP and infantile-onset HPP. Patients with HPP can exhibit symptoms of HPP including, but not limited to, skeletal deformity, hypotonia, mobility impairments, gait disturbance, bone deformity, joint pain, bone pain, bone fracture, muscle weakness, muscle pain, rickets (e.g., defects in growth plate cartilage), premature loss of deciduous teeth, incomplete bone mineralization, elevated blood and/or urine levels of phosphoethanolamine (PEA), PPi, pyridoxal 5'-phosphate (PLP), hypomineralization, rachitic ribs, hypercalciuria, short stature, HPP-related seizure, inadequate weight gain, craniosynostosis, and/or calcium pyrophosphate dihydrate crystal deposition (CPPD) in joints leading to, e.g., chondrocalcinosis and premature death. Symptoms of HPP can also include TBM and symptoms of TBM, such as cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent or continuous dyspnea, and recurrent bronchitis or pneumonia.

The terms "patient" or "subject" refer to a mammal, including, but not limited to, a human (e.g., a human having HPP, such as an infant) or a non-human mammal.

"Parenteral administration," "administered parenterally," and other grammatically equivalent phrases, as used herein, refer to a mode of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

By "pharmaceutically acceptable excipient, carrier, or diluent" is meant at least one excipient, carrier, or diluent, respectively, which is physiologically acceptable to the treated patient and which does not alter the therapeutic properties of an active agent (e.g., an sALP including an amino acid sequence having at least 95% sequence identity to the amino acid sequence of SEQ ID NO: 1, such as asfotase alfa) with which it is administered. One exemplary pharmaceutically acceptable carrier substance is physiological saline. For instance, the pharmaceutically acceptable carrier can include sodium chloride (e.g., 150 mM sodium chloride) and sodium phosphate (e.g., 25 mM sodium phosphate). Other physiologically acceptable excipients, carriers, and diluents, and their formulations, are known to those skilled in the art and described, e.g., in Remington: The Science and Practice of Pharmacy (22nd Ed), Allen (2012). For instance, a pharmaceutically acceptable excipient, carrier, or diluent can include dibasic sodium phosphate, heptahydrate; monobasic sodium phosphate, monohydrate; and sodium chloride at a pH between 7.2 and 7.6.

By "pharmaceutical composition" is meant a composition containing an active agent, such as an sALP (e.g., an sALP including an amino acid sequence having at least 95% sequence identity to the amino acid sequence of SEQ ID NO: 1, such as asfotase alfa), as described herein, formulated with at least one pharmaceutically acceptable excipient, carrier, or diluent. The pharmaceutical composition can be manufactured or sold with the approval of a governmental regulatory agency as part of a therapeutic regimen for the treatment or prevention of a disease or event (e.g., TBM) in a patient (e.g., an infant with HPP, such as an infant having perinatal-onset HPP, or an infant having infantile-onset HPP, or juvenile-onset HPP, or a patient having childhood-onset HPP). Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form. For example, an sALP (e.g., an sALP including an amino acid sequence having at least 95% sequence identity to the amino acid sequence of SEQ ID NO: 1, such as asfotase alfa) can be formulated as a pharmaceutical composition including dibasic sodium phosphate, heptahydrate; monobasic sodium phosphate, monohydrate; and sodium chloride at a pH between about 7.2 and 7.6.

The term "physiologically active," as used herein, refers to an sALP (e.g., an sALP including an amino acid sequence having at least 95% sequence identity to the amino acid sequence of SEQ ID NO: 1, such as asfotase alfa) that hydrolyzes phosphoethanolamine (PEA), inorganic pyrophosphate (PPi), and pyridoxal 5'-phosphate (PLP) to provide Pi, thereby decreasing extracellular concentrations of PEA, PPi, and PLP.

The terms "sALP," "soluble alkaline phosphatase," and "extracellular domain of an alkaline phosphatase" are used interchangeably and refer to a soluble, non-membrane bound ALP or a domain or a biologically active fragment of the soluble, non-membrane bound ALP. sALPs include, for example, an alkaline phosphatase lacking a C-terminal glycolipid anchor (GPI signal sequence, e.g., polypeptides including or consisting of the amino acid residues 18-502 of a human TNSALP (SEQ ID NOs: 2, 3, 4, 5, or 6)). In particular, a TNSALP may include, e.g., a polypeptide including or consisting of amino acid residues 1-485 of SEQ ID NO: 1, such as asfotase alfa, or a polypeptide variant having at least 95% sequence identity to the amino acid residues 1-485 of SEQ ID NO: 1. sALPs further include, for example, mammalian orthologs of human TNSALP, such as a rhesus TNSALP (SEQ ID NO: 7), a rat TNSALP (SEQ ID NO: 8), a canine TNSALP (SEQ ID NO: 9), a porcine TNSALP (SEQ ID NO: 10), a murine TNSALP (SEQ ID NO: 11), a bovine TNSALP (SEQ ID NOs: 12-14), or a feline TNSALP (SEQ ID NO: 15). sALPs also include soluble, non-membrane-bound forms of human PALP (e.g., polypeptides including or consisting of amino acid residues 18-502 of SEQ ID NOs: 16 or 17), GCALP (e.g., polypeptides including or consisting of amino acid residues 18-502 of SEQ ID NO: 18), and IALP (e.g., polypeptides including or consisting of amino acid residues 18-502 of SEQ ID NO: 19), and additional variants and analogs thereof that retain alkaline phosphatase activity, e.g., the ability to hydrolyze PP, such as variants having at least 90, 95, 97, or 99% sequence identity to any one of SEQ ID NOs: 7-19. An sALP, in particular, lacks the N-terminal signal peptide (e.g., aa 1-17 of SEQ ID NOs: 2-6, 8, 11-13, or 15 or aa 1-25 of SEQ ID NO: 7).

By "sALP fusion polypeptide" is meant a polypeptide having the structure Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V. In particular, the sALP fusion polypeptide can be Z-sALP-Y-spacer-X-$W_n$-V or Z-$W_n$-X-spacer-Y-sALP-V, such as hTNSALP-Fc-$D_{10}$ (e.g., asfotase alfa; SEQ ID NO: 1). Any one of X, Y, Z, V, the spacer, and/or $W_n$ can be absent or an amino acid sequence of at least one amino acid. For example, X, Y, Z, and V may be a dipeptide sequence (e.g., leucine-lysine or aspartic acid-isoleucine), such as a two residue linker at the Y position (e.g., leucine-lysine) and a two residue linker at the X position (e.g., aspartic acid-isoleucine). Spacers include, for example, a Fc region of an immunoglobulin, such as the amino acid sequence of SEQ ID NO: 20. $W_n$ can be a bone-targeting moiety as defined herein, e.g., having a series of consecutive aspartate (D) or glutamate (E) residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50.

As used herein, the term "sequence identity" refers to the percentage of amino acid (or nucleic acid) residues of a candidate sequence, e.g., an sALP, that are identical to the amino acid (or nucleic acid) residues of a reference sequence, e.g., the amino acid sequence of asfotase alfa (SEQ ID NO: 1), after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software, such as BLAST, BLAST-2, BLAST-P, BLAST-N, BLAST-X, WU-BLAST-2, ALIGN, ALIGN-2, CLUSTAL, or Megalign (DNASTAR) software. Those skilled in the art can determine appropriate parameters for measuring alignment, including any algorithms needed to achieve maximal alignment over the full length of the sequences being compared. For instance, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In particular, a reference sequence aligned for comparison with a candidate sequence can show that the candidate sequence exhibits from, e.g., 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to amino acid residues 1-17 of SEQ ID NOs: 2-6 or amino acid residues 1-25 of SEQ ID NO: 7.

The terms "tracheobronchomalacia" and "TBM" (which includes but is not limited to bronchomalacia, chondromalacia of the larynx, chondromalacia of the trachea, larangomalacia, laryngotracheobronchomalacia, and tracheomalacia), as used herein, refer to a rare condition characterized by softening or damage to the cartilaginous structures of the airway walls in the trachea and bronchi. In particular, TBM refers to the congenital form of the condition that can develop, e.g., during the perinatal period or infancy of a patient with HPP. TBM is characterized by symptoms including, but not limited to, cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent or continuous dyspnea, and recurrent bronchitis or pneumonia.

The term "tracheostomy," as used herein, refers to a surgical procedure performed to create an opening through the neck into the trachea of a patient (e.g., an HPP patient having TBM). A tube is usually placed through this opening to provide an airway and to remove mucus from the lungs of the patient.

By "therapeutically effective amount" is meant an amount of an sALP (e.g., an sALP including an amino acid sequence having at least 95% sequence identity to the amino acid sequence of SEQ ID NO: 1, such as asfotase alfa) that is sufficient to substantially improve, treat, prevent, delay, suppress, or arrest at least one symptom of TBM in an HPP patient (e.g., an infant with HPP, such as an infant having perinatal-onset HPP), such as cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent or continuous dyspnea, and recurrent bronchitis or pneumonia. A therapeutically effective amount of an sALP described herein can depend on the severity of TBM and the condition, weight, and general state of the patient and can be determined by an ordinarily-skilled artisan with consideration of such factors. A therapeutically effective amount of an sALP can be administered to an HPP patient having TBM in a dosage regimen as described herein over a period of time (e.g., at least one to six months, such as at least one year, at least two years, at least three years, at least four years, at least five years, at least six years, at least seven years, at least eight years, at least nine years, at least ten years, or longer).

By "treating," "treat," or "treatment" is meant the medical management of an HPP patient (e.g., infantile and perinatal-onset HPP patients) with the intent to cure, ameliorate, stabilize, reduce the likelihood of, or prevent TBM, e.g., by administering an sALP (e.g., an sALP including an amino acid sequence having at least 95% sequence identity to the amino acid sequence of SEQ ID NO: 1, such as asfotase alfa). Treatment can occur for a treatment period, in which an sALP is administered for a period of time (e.g., days, months, years, or longer) to treat an HPP patient having TBM. This term includes active treatment directed toward the improvement of TBM in an HPP patient; symptomatic treatment directed toward symptoms of TBM in an HPP patient; preventative treatment directed to minimizing the development of TBM in an HPP patient, e.g., in an HPP patient who does not yet have TBM, but who is susceptible to or at risk of developing TBM; and supportive treatment employed to supplement another specific therapy directed toward the improvement of TBM in an HPP patient.

The term "ventilator support," as used herein, refers to artificial ventilation of an HPP patient (e.g., infantile and perinatal-onset HPP patients) having TBM in which mechanical means, in particular, a ventilator, are used to assist or replace spontaneous breathing. For example, ventilator support of an HPP patient exhibiting symptoms of TBM or likely to have TBM can be required prior to treatment with an sALP (e.g., an sALP including an amino acid sequence having at least 95% sequence identity to the amino acid sequence of SEQ ID NO: 1, such as asfotase alfa), such as administration of an sALP in a dosage regimen providing greater than or equal to about 6 mg/kg/week of the sALP to the patient. For example, ventilator support of an HPP patient exhibiting symptoms of TBM or likely to have TBM can be required during treatment with an sALP, and the ventilator support may help maintain patency of the airways of the HPP patient. The HPP patient can exhibit decreased reliance on ventilator support, can maintain airway patency without ventilator support, or can no longer require ventilator support after administration of the sALP, such as after administration of the sALP for a treatment period of at least one year, at least two years, at least three years, at least four years, at least five years, at least six years, at least seven years, at least eight years, at least nine years, at least ten years, or longer.

BRIEF DESCRIPTION OF THE DRAWINGS

FIG. 1 shows the amino acid sequence of asfotase alfa (STRENSIQ®, Alexion Pharmaceuticals, Inc., SEQ ID NO: 1).

FIGS. 2A-2B show radiographic images of the HPP patient's chest prior to treatment with asfotase alfa. FIG. 2C shows a radiographic image of the HPP patient's chest after treatment with asfotase alfa at a dose of 1.3 mg/kg (7.8 mg/kg/week). FIG. 2D shows a radiographic image of the HPP patient's chest after treatment with asfotase alfa at a dose of 2.5 mg/kg (7.5 mg/kg/week).

DETAILED DESCRIPTION

Figure 2A:
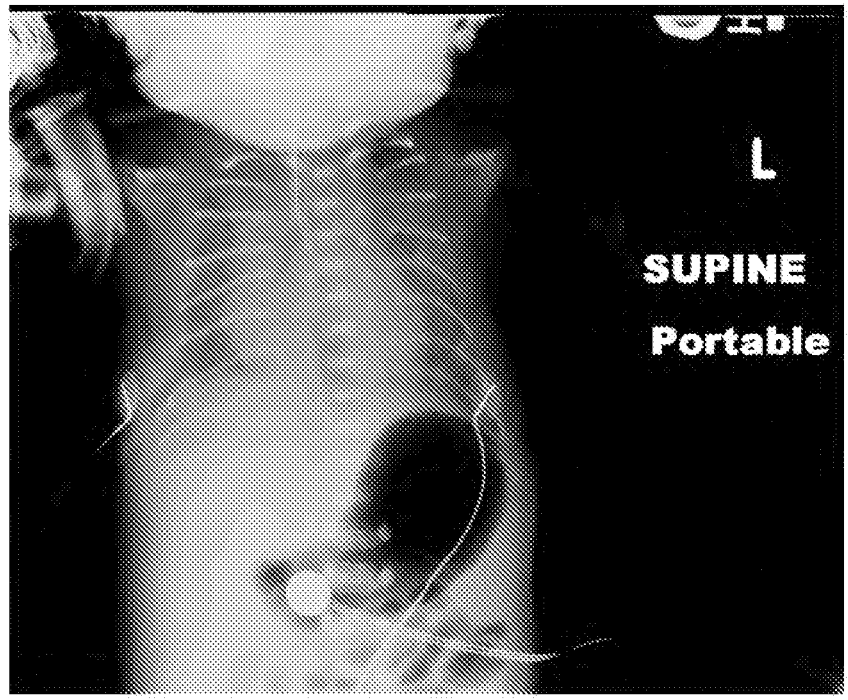
FIGS. 2A-2D are radiograph images of the chest of a hypophosphatasia (HPP) patient with tracheobronchomalacia (TBM) at birth (FIG. 2A), 16 days (FIG. 2B), 9 months (FIG. 2C), and 12 months (FIG. 2D).

Patients with hypophosphatasia (HPP), particularly infants, can exhibit respiratory compromise due to tracheobronchomalacia (TBM), often requiring assisted ventilator support and positive airway pressure in order to survive. We have discovered that asfotase alfa (SEQ ID NO: 1, STRENSIQ®, Alexion Pharmaceuticals, Inc.) can be used effectively to treat and/or ameliorate TBM, its symptoms, and decreased respiratory function associated therewith in HPP patients (e.g., humans having HPP). In particular, asfotase alfa is effective for the treatment of TBM and symptoms thereof in infants having HPP, such as infants having perinatal-onset HPP and/or infantile-onset HPP, when administered in a dosage regimen that provides greater than or equal to about 6 mg/kg/week of asfotase alfa to the infant in need thereof.

Methods for administering asfotase alfa (SEQ ID NO: 1) to an HPP patient in need thereof (e.g., infantile-onset HPP patients and perinatal-onset HPP patients) that result in an improvement in TBM are described. For example, asfotase alfa can be administered to an HPP patient exhibiting one or more symptoms of TBM including, but not limited to, cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent or continuous dyspnea, and recurrent bronchitis or pneumonia.

The HPP patient can exhibit an improvement in one or more of the symptoms of TBM following administration of asfotase alfa for a treatment period of, e.g., about one week, about two weeks, about three weeks, about one month, about two months, about three months, about four months, about five months, about six months, about seven months, about eight months, about nine months, about ten months, about eleven months, or about one year. Accordingly, administration of asfotase alfa can decrease the reliance of the HPP patient on ventilator support, or can eliminate the need for ventilator support altogether. Moreover, treatment with asfotase alfa can increase survival of the HPP patient with TBM.

The methods of treatment can also include administering asfotase alfa to an HPP patient in combination with a medical procedure (e.g., a tracheostomy or a bronchoscopy). Asfotase alfa can be administered to the patient prior to, or after, the medical procedure (e.g., a tracheostomy or a bronchoscopy).

Given the results described herein using asfotase alfa, other sALPs (such as a polypeptide variant having at least 95% sequence identity to the sequence of SEQ ID NO: 1) can be used to treat TBM or one or more symptoms thereof in HPP patients (e.g., infantile and perinatal-onset HPP patients).

The methods of treatment, alkaline phosphatases, and pharmaceutical compositions are described herein.

Methods of Treatment

The methods described herein can be used to treat TBM or one or more symptoms of TBM in HPP patients, such as infants having HPP (e.g., perinatal-onset HPP patients). Accordingly, an sALP can be administered to an HPP patient presenting one or more symptoms of TBM at birth or subsequent to birth. In particular, the HPP patient (e.g., infantile and perinatal-onset HPP patients) treated for TBM can be one that has not previously been treated with the sALP.

For example, TBM or one or more symptoms of TBM can be treated by administering an sALP to infants having HPP across a range of ages, e.g., about one day to about 1 month old, about 5 days to about 6 months old, about 10 days to about 8 months old, about 10 days to about 1 year old, about 1 month to about 6 months old, about 2 weeks to about 4 months old, about 3 months to about 9 months old, about 3 weeks to about 10 months old, about 3 months to about 16 months old, about 2 months to about 22 months old, about 7 weeks to about one year old, about 5 weeks to about 15 months old, about 5 months to about 17 months old, about 6 months to about 18 months old, or about 2 months to about 3 years old.

Symptoms of TBM

An HPP patient in need of treatment can exhibit one or more symptoms of TBM, e.g., relative to a healthy subject of about the same age and/or gender, prior to administration of an sALP. Symptoms that can be used to diagnose TBM prior to treatment with an sALP or that signify an HPP patient in need of treatment can include, but are not limited to, cardio-respiratory arrest, tracheostomy, cardiac arrest, respiratory distress (e.g., difficulty in breathing), sputum retention (e.g., mucus in the lower airways of the trachea and bronchi), wheezing, coughing, anoxic spells, cyanosis (e.g., the abnormal blue discoloration of the skin and mucous membranes), bradycardia (e.g., a slow heart rate), tachyarrhythmia (e.g., a heart rate that exceeds the resting rate of a healthy subject), spontaneous hyperextension of the neck, prolonged expiratory breathing phase, failure to thrive, sternal retractions (e.g., indrawing of the abdomen at the sternum or breastbone), substernal retractions (e.g., indrawing of the abdomen just below the sternum or breastbone), intercostal retractions (e.g., indrawing of the skin in between each rib), intermittent or continuous dyspnea (e.g., difficult or laboured breathing), and recurrent bronchitis or pneumonia. Following administration of an sALP, such as in a dosage regimen providing greater than or equal to about 6 mg/kg/week, an HPP patient can exhibit an improvement in one or more symptoms of TBM.

Administration of an sALP

The method of treatment involves administering an sALP to treat TBM or one or more symptoms thereof in an HPP patient (e.g., infantile and perinatal-onset HPP patients) in a dosage regimen providing greater than or equal to about 6 mg/kg/week of the sALP (e.g., about 7 mg/kg/week to about 25 mg/kg/week of the sALP) to the patient. In particular, a dosage regimen to treat TBM in an HPP patient can provide, e.g., about 6.5 mg/kg/week of the sALP, about 7 mg/kg/week of the sALP, about 7.5 mg/kg/week of the sALP, about 7.8 mg/kg/week of the sALP, about 8 mg/kg/week of the sALP, about 8.5 mg/kg/week of the sALP, about 9 mg/kg/week of the sALP, about 10 mg/kg/week of the sALP, about 10.5 mg/kg/week of the sALP, about 11 mg/kg/week of the sALP, about 11.5 mg/kg/week of the sALP, about 12 mg/kg/week of the sALP, about 12.5 mg/kg/week of the sALP, about 13 mg/kg/week of the sALP, about 13.5 mg/kg/week of the sALP, about 14 mg/kg/week of the sALP, about 14.5 mg/kg/week of the sALP, about 15 mg/kg/week of the sALP, about 16 mg/kg/week of the sALP, about 17 mg/kg/week of the sALP, about 18 mg/kg/week of the sALP, about 19 mg/kg/week of the sALP, about 20 mg/kg/week of the sALP, about 21 mg/kg/week of the sALP, about 22 mg/kg/week of the sALP, about 23 mg/kg/week of the sALP, about 24 mg/kg/week of the sALP, or about 25 mg/kg/week of the sALP to the patient.

For example, the dosage regimen can include administering about 3 mg/kg of the sALP three times a week, about 2.5 mg/kg of the sALP three times a week, about 1.3 mg/kg of the sALP six times a week, or about 5 mg/kg of the sALP three times a week. Moreover, an sALP can be administered to treat TBM or one or more symptoms of TBM in an HPP patient in any of the dosage regimens described herein for a treatment period of least one year (e.g., at least two years, at least three years, at least four years, at least five years, at least six years, at least seven years, at least eight years, at least nine years, at least ten years, or longer than ten years, such as for the lifetime of the patient).

When administration of an sALP does not result in an improvement in one or more symptoms of TBM, the dosage regimen can be modified (e.g., increased or decreased) until an effective amount of the sALP to treat TBM or one or more symptoms of TBM in the HPP patient (e.g., infantile and perinatal-onset HPP patients) is identified. For instance, the dosage of an sALP can be increased to provide greater than or equal to about 6 mg/kg/week, as discussed above, when the HPP patient (e.g., infantile and perinatal-onset HPP patients) does not exhibit an improvement in one or more symptoms of TBM after a treatment period of, e.g., at least two weeks, three weeks, one month, two months, three months, four months, five months, or six months.

An sALP can also be administered prior to, simultaneously, or following administration of a second active agent. In particular, second active agents for use in the methods of treatment include, but are not limited to, opioids (e.g., methadone, codeine, lydrocodone, fentanyl, hydromorphone, morphine, and oxycodone), anti-anxiety drugs (e.g., alprazolam, midazolam, clobazam, clonazepam, clorazepate, diazepam, duloxetine, fluoxetine, escitalopram, lorazepam, nitrazepam, temazepam, and nimetazepam), antidepressants (e.g., desipramine, amitriptyline, agomelatine, etoperidone, and phenelzine), anti-convulsant drugs (e.g., lithium carbonate, lithium citrate, topiramate, oxcarbazepine, and valproic acid), antipsychotics (e.g., aripiprazole, clozapine, risperidone, asenaphine, and olanzapine), nonsteroidal anti-inflammatory drugs (e.g., aspirin, ibuprofen, ketoprofen, ketorolac tromethamine, and naproxen), corticosteroids (e.g., prednisolone, methylprednisolone, hydrocortisone, amcinonide, fluocinonide, flunisolide, prednicarbate, betamethasone, and triamcinolone acetonide), and muscle relaxants (e.g., carisoprodol, cyclobenzaprine, and diazepam). Administration of the second active agent can be discontinued or the dosage can be reduced once the HPP patient exhibits an improvement in one or more symptoms of TBM following administration of an sALP.

Additional Medical Procedures

An HPP patient in need of treatment can require ventilation prior to administration of an sALP (e.g., an sALP including an amino acid sequence having at least 95% sequence identity to the amino acid sequence of SEQ ID NO: 1, such as asfotase alfa) to treat TBM. In particular, the HPP patient can require assisted ventilation, including but not limited to one or more of high-frequency oscillation, continuous positive airway pressure (CPAP) ventilation, positive end-expiratory pressure (PEEP) ventilation, bilevel or biphasic positive airway pressure (BiPAP), and intermittent positive pressure ventilation (IPPV). Assisted ventilation can be required to maintain patency of the airways during treatment with an sALP, and may be adjusted in strength and type in order to maintain sufficient airway patency during treatment. PEEP can be required in HPP patients exhibiting greater TBM severity. For example, an HPP patient with TBM can require PEEP ventilation of about 5 cm $H_2O$ to about 15 cm $H_2O$, such as 5 cm $H_2O$, 6 cm $H_2O$, 7 cm $H_2O$, 8 cm $H_2Or$, 9 cm $H_2O$, 10 cm $H_2O$, 11 cm $H_2O$, 12 cm $H_2O$, 13 cm $H_2O$, 14 cm $H_2O$, or 15 cm $H_2O$.

Administration of an sALP to treat TBM in an HPP patient in a dosage regimen as described herein can result in the patient exhibiting decreased reliance on ventilator support. For example, administration of asfotase alfa in a dosage regimen providing greater than or equal to 6 mg/kg/week for a treatment period of about one month, about two months, about three months, about four months, about five months, about six months, about seven months, about eight months, about nine months, about ten months, or longer can reduce or eliminate the need for support. For example, administration of an sALP can result in a decrease in the PEEP required by the HPP patient of, e.g., about 1 cm $H_2O$, about 2 cm $H_2O$, about 3 cm $H_2O$, about 4 cm $H_2O$, about 5 cm $H_2O$, about 6 cm $H_2O$, about 7 cm $H_2O$, about 8 cm $H_2O$, about 9 cm $H_2O$, about 10 cm $H_2O$, or more. Additionally, after administration of an sALP in a dosage regimen providing greater than or equal to 6 mg/kg/week, the HPP patient in need thereof can receive continuous positive airway pressure (CPAP) ventilation instead of positive end-expiratory pressure (PEEP) ventilation or bilevel or biphasic positive airway pressure (BiPAP), or may no longer require ventilator support at all.

HPP patients (e.g., infantile and perinatal-onset HPP patients) can be diagnosed with TBM prior to administration of an sALP using bronchoscopy (e.g., flexible bronchoscopy and/or microlaryngobronchoscopy). For example, bronchoscopy can be performed on an HPP patient at the age of one day, two days, three days, four days, five days, six days, one week, two weeks, three weeks, one month, two months, three months, four months, five months, six months, seven months, eight months, nine months, ten months, eleven months, one year, or older. In particular, bronchoscopy of an HPP patient can show, e.g., softened airways, collapse of the trachea and bronchi, dynamic bronchial collapse during restful breathing, narrowing of the subglottic space, cervical tracheomalacia, laryngotracheobronchomalacia, and/or suprastomal tracheal collapse. Bronchoscopy can also be performed on the patient after a treatment period of, e.g., about one week, about two weeks, about three weeks, about one month, about two months, about three months, about four months, about five months, about six months, about seven months, about eight months, about nine months, about ten months, about eleven months, or about one year, to determine if the amount of the sALP administered is therapeutically effective.

The method of treatment can further include performing tracheostomy in combination with administration of an sALP in a dosage regimen that provides greater than or equal to 6 mg/kg/week of the sALP to treat TBM or one or more symptoms of TBM in an HPP patient (e.g., infantile and perinatal-onset HPP patients). Tracheostomy can be performed in combination with administration of an sALP to treat TBM in an HPP patient at, e.g., about one week, about two weeks, about three weeks, about one month, about two months, about three months, about four months, about five months, about six months, about seven months, about eight months, about nine months, about ten months, about eleven months, or about one year of age.

The method can involve administering the sALP to the HPP patient prior or after performing a tracheostomy, e.g., to provide long-term ventilation to the airways and/or remove mucus from the lungs of the HPP patient. For example, the method of treatment can include increasing the dosage of an sALP after performing the tracheostomy if the patient does not exhibit an improvement in one or more of the symptoms of TBM following administration of the sALP for a treatment period of, e.g., at least two weeks, three weeks, one month, two months, three months, four months, five months, or six months.

Additionally, the method can include performing gastrostomy in combination with administration of an sALP in a dosage regimen that provides greater than or equal to 6 mg/kg/week of the sALP to treat TBM or one or more symptoms of TBM in an HPP patient (e.g., infantile and perinatal-onset HPP patients). Gastrostomy can be performed in combination with administration of an sALP to treat TBM in an HPP patient at, e.g., about one week, about two weeks, about three weeks, about one month, about two months, about three months, about four months, about five months, about six months, about seven months, about eight months, about nine months, about ten months, about eleven months, or about one year of age.

Alkaline Phosphatase

Asfotase alfa is a human tissue non-specific alkaline phosphatase (TNSALP; SEQ ID NO: 1) fusion polypeptide formulated for the treatment of HPP. In particular, asfotase alfa can be used effectively to treat TBM and symptoms associated therewith in HPP patients (e.g., infantile and perinatal-onset HPP patients) in a dosage regimen that provides greater than or equal to 6 mg/kg/week of the sALP to the patient.

The treatment methods are not limited to administration of a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, $PP_i$). There are four known mammalian alkaline phosphatase (ALP) isozymes: tissue nonspecific alkaline phosphatase (TNSALP; described further below), placental alkaline phosphatase (PLALP; e.g., Accession Nos. P05187, NP_112603, and NP_001623), germ cell alkaline phosphatase (GALP; e.g., Accession No. P10696), and intestinal alkaline phosphatase (IALP; e.g., Accession Nos. P09923 and NP_001622). Any of these isozymes could potentially be used to treat TBM according to the methods described herein.

In addition to the exemplary ALPs discussed above, any polypeptide having the identical or similar catalytic site structure and/or enzymatic activity of ALP can be used (e.g., as an sALP or an sALP fusion polypeptide as defined herein) for treating TBM or symptoms of TBM in HPP patients, such as infants with HPP. For example, sALP constructs that can be used to treat TBM in an HPP patient include, e.g., the bone delivery conjugates described in PCT publication Nos. WO 2005/103263 and WO 2008/138131, incorporated herein by reference.

TNSALPs that can be administered according to the methods described herein include, e.g., human TNSALP (Accession Nos. NP_000469, AAI10910, AAH90861, AAH66116, AAH21289, and AAI26166); rhesus TNSALP (Accession No. XP_01109717); rat TNSALP (Accession No. NP_037191); dog TNSALP (Accession No. AAF64516); pig TNSALP (Accession No. AAN64273); mouse (Accession No. NP_031457); cow TNSALP (Accession Nos. NP_789828, NP_776412, AAM 8209, and AAC33858); cat TNSALP (Accession No. NP_001036028); and variants thereof having 90, 95, 97, or 99% sequence identity to any one of SEQ ID NOs: 7-19. In particular, TNSALP can be a recombinant human TNSALP (e.g., SEQ ID NO: 1, asfotase alfa; see U.S. Pat. Nos. 7,763,712 and 7,960,529, incorporated herein by reference in their entirety) used for the treatment of TBM or one or more symptoms of TBM in HPP patients (e.g., an infantile or perinatal-onset HPP patient). The TNSALP can also be one that exhibits at least about 95% sequence identity to the polypeptide or nucleic acid sequence of the above-noted TNSALPs.

Soluble Alkaline Phosphatases

ALPs that can be used in the methods described herein include soluble (e.g., extracellular or non-membrane-bound) forms of any of the ALPs described herein. The methods are not limited to a particular sALP and can include any sALP that is physiologically active toward, e.g., phosphoethanolamine (PEA), inorganic pyrophosphate (PPi), and pyridoxal 5'-phosphate (PLP). In particular, an sALP is one that is catalytically competent to improve skeletal mineralization in bone. Nucleic acids encoding the sALPs described herein can also be used in the methods for treating TBM or one or more symptoms of TBM in HPP patients (e.g., infantile or perinatal-onset HPP patients).

An example of an ALP that can be produced as an sALP is TNSALP (e.g., human TNSALP (hTNSALP)). TNSALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNSALP are extracellular.

In particular, TNSALP can be engineered to replace the first amino acid of the hydrophobic C-terminal sequence (an alanine) with a stop codon, thereby producing an engineered hTNSALP that contains all amino acid residues of the native anchored form of TNSALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNSALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNSALP also has an N-terminal signal peptide sequence. The N-terminal signal peptide is present on the synthesized protein when it is synthesized, but cleaved from TNSALP after translocation into the ER. The sALPs include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (J. Mol. Biol. 340(4):783-795, 2004) and/or at www.cbs.dtu.dk/services/SignalP/.

sALP consensus sequences derived from the extracellular domain of ALP isozymes (e.g., TNSALP, PALP, GCALP, or IALP) can also be used to produce an sALP for treatment of TBM according to the methods described herein. Thus, similar to sTNSALP discussed above, other soluble human ALP isozymes, i.e., those without the peptide signal and preferably comprising the extracellular domain of the ALPs, can be used in the methods. The sALPs also include polypeptide sequences satisfying a consensus sequence derived from the ALP extracellular domain of human ALP isozymes and of mammalian TNSALP orthologs (human, mouse, rat, cow, cat, and dog) or a consensus derived from the ALP extracellular domain of just mammalian TNSALP orthologs (human, mouse, rat, cow, cat, and dog). The sALPs also include those which satisfy similar consensus sequences derived from various combinations of these TNSALP orthologs or human ALP isozymes. Such consensus sequences are described, for example, in WO 2008/138131.

sALPs of the present methods can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., SEQ ID NOs: 1-24; for example the sALP fusion polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Patent Application Publication No. 2013/0323244, hereby incorporated by reference in its entirety. An sALP can optionally be glycosylated at any appropriate one or more amino acid residues. An sALP can have 1, 2, 3, 4, 5, 6, 7, 8, 9, 10, or more additions, deletions, or substitutions relative to any of the sALPs described herein (such as TNSALP, for example the sALP fusion polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs, linkers, spacers (e.g., Fc regions), and bone-targeting moieties described herein can be combined in a fusion polypeptide, which includes the structures Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V. In particular, the structure of the sALP fusion polypeptide can be Z-sALP-Y-spacer-X-$W_n$-V or Z-$W_n$-X-spacer-Y-sALP-V. The sALP of the sALP fusion polypeptide can be the full-length ALP or functional fragments of ALPs, such as the soluble, extracellular domain of the ALP, as is described herein (e.g., TNSALP, PALP, GCALP and IALP).

Any one of X, Y, Z, and V and/or the spacer can be absent or a linker region including an amino acid sequence of at least one amino acid. For example, X, Y, Z, and V may be a dipeptide sequence (e.g., leucine-lysine or aspartic acid-isoleucine), such as a two residue linker at the Y position (e.g., leucine-lysine) or a two residue linker at the X position (e.g., aspartic acid-isoleucine). For example, sALP fusion polypeptides can have the structure hTNSALP-Fc-Dio (e.g., an sALP including an amino acid sequence having at least 95% sequence identity to the amino acid sequence of SEQ ID NO: 1, such as asfotase alfa).

The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at one or more amino acid residues. Additionally, a linker as described herein can include any other sequence or moiety, attached covalently or non-covalently. The linker can also be absent, in which the spacer (e.g., the Fc region) and the sALP are fused together directly, with no intervening residues.

Useful spacers include, but are not limited to, polypeptides including a Fc region. For example, an sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences) fragments. Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human).

For instance, the Fc fragment is human IgG-1. The Fc fragments can include, for example, the CH2 and CH3 domains of the heavy chain and any portion of the hinge region. The Fc region can optionally be glycosylated at any appropriate one or more amino acid residues known to those skilled in the art. In particular, the Fc fragment of the fusion polypeptide has the amino acid sequence of SEQ ID NO: 20, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 20. Engineered, e.g., non-naturally occurring, Fc regions can be incorporated into the sALP fusion polypeptides described herein. Examples of engineered Fc regions are described in, e.g., International Application Pub. No. WO2005/007809, which is hereby incorporated by reference. An Fc fragment as described herein can have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

$W_n$ can be a bone-targeting moiety, e.g., having a series of consecutive aspartate (D) or glutamate (E) residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the linker region. For instance, the bone-targeting moiety can be present at the C-terminal end of an sALP fusion polypeptide. sALP fusion polypeptides can also lack a bone-targeting moiety.

The sALP fusion polypeptides (e.g., including a sALP variant having at least 95% sequence identity to the sequence of SEQ ID NO: 1, such as asfotase alfa) can be associated into dimers or tetramers. For example, two sALP-Fc monomers can covalently be linked through two disulfide bonds located in the hinge regions of the Fc fragments. Additionally, the sALP fusion polypeptide can be glycosylated or PEGylated.

Production of Nucleic Acids and Polypeptides

The nucleic acids encoding an sALP (e.g., an sALP including an amino acid sequence having at least 95% sequence identity to the amino acid sequence of SEQ ID NO: 1, such as asfotase alfa) can be produced by any method known in the art. Typically, a nucleic acid encoding the desired polypeptide is generated using molecular cloning methods, and is generally placed within a vector, such as a plasmid or virus. The vector can be used, e.g., transform the nucleic acid into a host cell appropriate for the expression of the fusion polypeptide. Representative methods are disclosed, for example, in Maniatis et al. (Cold Springs Harbor Laboratory, 1989).

Many cell types can be used as appropriate host cells, although mammalian cells are preferable because they are able to confer appropriate post-translational modifications. Host cells can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media (i.e., HYCLONE™, GE Healthcare; SFM4CHO, Sigma CHO DHFR⁻; Cambrex POWER™ CHO CD supplemented with 2-4 mM L-glutamine, etc.). These media are desirably prepared without thymidine, hypoxanthine and L-glycine to maintain selective pressure, allowing stable protein-product expression.

Pharmaceutical Compositions

A composition including an sALP that can be used in the methods (e.g., an sALP including an amino acid sequence having at least 95% sequence identity to the amino acid sequence of SEQ ID NO: 1, such as asfotase alfa) can be administered by a variety of methods known in the art. For example, asfotase alfa (SEQ ID NO: 1) can be administered at a range of dosages, in a variety of formulations, and in combination with pharmaceutically acceptable excipients, carriers, or vehicles. In particular, asfotase alfa is a sterile, preservative-free, nonpyrogenic, clear, slightly opalescent or opalescent, colorless to slightly yellow, with few small translucent or white particles, aqueous solution that is formulated for, e.g., subcutaneous administration. Asfotase alfa can be supplied in glass single-use vials containing asfotase alfa in combination with dibasic sodium phosphate, heptahydrate; monobasic sodium phosphate, monohydrate; and sodium chloride at a pH between 7.2 and 7.6.

Dosage

A pharmaceutical composition including an sALP can be formulated for administration to HPP patients (e.g., infantile and perinatal-onset HPP patients) having TBM or one or more symptoms of TBM at a range of dosages. The dosages will depend on many factors including the mode of administration and the age of the patient (e.g., three years old or younger). Typically, the amount of the composition including an sALP contained within a single dose will be an amount that is effective to treat TBM or symptoms of TBM as described herein without inducing significant toxicity.

For example, an sALP can be formulated for administration to HPP patients having TBM or one or more symptoms of TBM, in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of an sALP include, but are not limited to, 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. Dosages of compositions including sALPs can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be formulated for administration, e.g., twice, three times, four times, five times, six times, seven times, eight times, nine times, 10 times, 11 times, or 12 times per day. In particular, the dosing regimen is once weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), month(s), or even for the remaining lifespan of the HPP patient having TBM or one or more symptoms of TBM (e.g., an infantile or perinatal-onset HPP patient).

An sALP can be formulated as a solution for injection, which is a clear, colorless to slightly yellow, aqueous solution, pH 7.4. The sALP may be formulated at a concentration of 12 mg/0.3 mL, 18 mg/0.45 mL, 28 mg/0.7 mL, 40 mg/1 mL, or 80 mg/0.8 mL. For example, the composition can be formulated as a 40 mg/ml solution for injection, in which each ml of solution contains 40 mg of sALP (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). Additionally, an sALP can be formulated as a solution for injection at a concentration of 100 mg/ml, in which each 1 ml of solution contains 100 mg of sALP (e.g., each vial contains 0.8 ml solution and 80 mg of asfotase alfa (100 mg/ml)).

For example, a dosage of an sALP can be 2 mg/kg of body weight administered subcutaneously three times per week, or 1 mg/kg of body weight administered subcutaneously six times per week. Additional dosage information is provided below (Table 1).

TABLE 1

DOSING OF ASFOTASE ALFA

| | If injecting 3x per week | | | If injecting 6x per week | | |
|---|---|---|---|---|---|---|
| Body Weight (kg) | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0.40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.30 ml | 0.3 ml |
| 13 | 26 mg | 0.65 ml | 0.7 ml | 13 mg | 0.33 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |
| 18 | 36 mg | 0.90 ml | 1 ml | 18 mg | 0.45 ml | 0.45 ml |
| 19 | 38 mg | 0.95 ml | 1 ml | 19 mg | 0.46 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |

TABLE 1-continued

DOSING OF ASFOTASE ALFA

| | If injecting 3x per week | | | If injecting 6x per week | | |
|---|---|---|---|---|---|---|
| Body Weight (kg) | Dose to be injected | Volume to be injected | Vial type used for injection | Dose to be injected | Volume to be injected | Vial type used for injection |
| 80 | | | | 80 mg | 0.80 ml | 0.8 ml |
| 90 | | | | 90 mg | 0.90 ml | 0.8 ml (x2) |
| 100 | | | | 100 mg | 1.00 ml | 0.8 ml (x2) |

Formulations

A composition including a sALP (e.g., an sALP including an amino acid sequence having at least 95% sequence identity to the amino acid sequence of SEQ ID NO: 1, such as asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes, and suppositories. For example, compositions intended for systemic or local delivery can be in the form of injectable or infusible solutions. Accordingly, the sALP compositions can be formulated for administration by a parenteral mode (e.g., subcutaneous, intravenous, intraperitoneal, or intramuscular injection).

The sALP compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

Preparations containing an sALP can be provided to an HPP patient having TBM or one or more symptoms of TBM (e.g., an infant with HPP, such as an infant having perinatal-onset HPP), in combination with pharmaceutically acceptable excipients, carriers, or diluents. Examples of non-aqueous excipients, carriers, or diluents are propylene glycol, polyethylene glycol, vegetable oil, fish oil, and injectable organic esters. Aqueous excipients, carriers, or diluents include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils.

Pharmaceutically acceptable salts can also be included in the sALP compositions, such as mineral acid salts including hydrochlorides, hydrobromides, phosphates, sulfates, and the salts of organic acids (e.g., acetates, propionates, malonates, and benzoates). For example, the pharmaceutically acceptable carrier can include sodium chloride and/or sodium phosphate, in which the composition includes, e.g., about 150 mM sodium chloride and/or about 25 mM sodium phosphate, pH 7.4.

Compositions including an sALP can also be formulated with pharmaceutically acceptable excipients, carriers, or diluents that will protect the sALP composition against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) *Sustained and Controlled Release Drug Delivery Systems*, Marcel Dekker, Inc., New York.

The following examples are intended to illustrate, rather than limit, the disclosure. These studies feature the administration of asfotase alfa (SEQ ID NO: 1) at, e.g., a dosage regimen of greater than or equal to 6 mg/kg/week, to treat tracheobronchomalacia (TBM) and symptoms thereof in patients with HPP.

EXAMPLES

Example 1. Overview of Tracheobronchomalacia (TBM) Cases

Treatment of tracheobronchomalacia (TBM) in 3 infants having hypophosphatasia (HPP) with asfotase alfa was initiated as part of a clinical trial and one under a compassionate use program. Four HPP patients with TBM (2 female and 2 male) were identified and treated with a soluble alkaline phosphatase (sALP) composition (STRENSIQ™ (asfotase alfa); SEQ ID NO: 1 as shown in FIG. 1). Key inclusion criteria for the clinical trial included a patient age of 5 years old or younger with onset of HPP symptoms at less than 6 months old and low alkaline phosphatase (ALP) levels, high pyridoxal 5'-phosphate (PLP) levels, and radiographic evidence of HPP.

Additional inclusion criteria for the clinical trial included two or more of the following: non-traumatic post-natal fracture or delayed fracture healing, nephrocalcinosis or history of elevated serum calcium, functional craniosynostosis, respiratory compromise or rachitic chest deformity, pyridoxine (vitamin B6)-responsive seizures, and failure to thrive. Key exclusion criteria included serum calcium or phosphate levels below the normal range, serum 25-hydroxy vitamin D levels less than 20 ng/mL, and previous treatment with bisphosphonates. HPP diagnosis in each of the patients was confirmed by serum biochemistry analysis (e.g., ALP levels), supplemented by physical examination and skeletal survey. Mutations in the ALPL gene were found in all four patients as described herein.

Initial medical problems associated with HPP in these four patients included respiratory distress requiring respiratory support. TBM was identified by direct laryngotracheobronchoscopy or flexible bronchoscopy between two and five months of age. Respiratory support requirements were defined as mechanical ventilation via intubation or tracheostomy and ventilation by continuous positive airway pressure (CPAP) or intermittent positive pressure (IPP) ventilation. Requirements for positive-end expiratory pressure (PEEP) were also noted. Peak inspiratory pressure (PIP) was also measured.

All patients were treated with asfotase alfa at two months old or younger at a dosage of 6 mg/kg/week to 15 mg/kg/week. At birth, all four patients required ventilation with subsequent tracheostomy for long-term ventilation with PEEP. All patients experienced frequent episodes of profound desaturations and bradycardia, and three patients experienced cardio-respiratory arrests. When the patients were 15 to 24 months old, the TBM had resolved in two patients (off ventilator support), partially resolved in one patient (27 months old, ventilator support) and remained significant in one patient (23 months old, tracheostomy in situ). Without asfotase alfa treatment, these infants would not likely have survived to one year of age and there is little chance that their airways would have matured. Of the four patients treated, two patients experienced complete resolution of TBM, and one patient experienced partial resolution of TBM, within two years of birth. An overview of treatment and patient outcomes based on these studies featuring treatment with asfotase alfa is shown in Table 2.

TABLE 2

Overview of treatment and patient outcomes during.

| | Patient 1 | Patient 2 | Patient 3 | Patient 4 |
|---|---|---|---|---|
| Pharmaceutical treatments | 1 mo 1 d: Asfotase alfa 6 mg/kg/wk<br>2 mo 24 d: Asfotase alfa 9 mg/kg/wk | 5 wk: Asfotase alfa 6 mg/kg/wk<br>4 mo: Lorazepam and morphine for sedation<br>6 mo: Asfotase alfa 7.8 mg/kg/wk<br>9 mo: Asfotase alfa 7.5 mg/kg/wk<br>9.5 mo: 9 mg/kg/wk | 7 wk 4 d: Asfotase alfa 6 mg/kg/wk<br>5 wk: Lorazepam 0.05 mg/kg every 6 h (for agitation)<br>4 mo: Methadone (for sedation and pain) and continued lorazepam<br>6 mo: Methadone weaned, midazolam added for agitation<br>3 yr, 4 mo. 12 mg/kg/wk | 1 mo: Asfotase alfa 6 mg/kg/wk<br>3 mo 14 d (post-cardiac arrest): Asfotase alfa 15 mg/kg/wk<br>3 yr, 11 mo.: Asfotase alfa 2.5 mg/kg/wk |
| Surgical treatments | 1 mo 8 d: Tracheostomy | 6 wk: Tracheostomy<br>4 mo: Gastrostomy | 7 wk: Tracheostomy<br>3 mo: Gastrostomy | 1 mo 15 d: Tracheostomy<br>1 yr Gastrostomy |
| Age at TBM diagnosis | 2 mo | 5 mo | 6 mo (suspected at 8 wk) | 5 mo |
| Additional findings | 1 mo: CPAP with PEEP (5 cm $H_2O$)<br>1 mo 2 d: Change from CPAP to IPPV PEEP and central venous line insertion; PEEP (8 cm $H_2O$)<br>1 mo 5 d: PEEP (10 cm $H_2O$)<br>2 mo: Severe TBM identified; PEEP (12 cm $H_2O$)<br>9 mo: Flexible DLTB revealed normal patency of larynx, trachea, and left main bronchus; residual left bronchomalacia required PEEP (6 cm $H_2O$)<br>12 mo: Repeat DLTB revealed resolution of TBM, with mild left bronchomalacia; weaned to CPAP; PEEP (5 cm $H_2O$) | 3 mo: Respiratory arrest requiring bag and mask positive pressure ventilation<br>4 and 6 mo: Cardio-respiratory arrest<br>5 mo: MLB revealed Grade 3 stenosis of subglottis; flexible bronchoscopy revealed narrowed subglottic space and severe cervical tracheomalacia<br>10 mo: TBM improved with mild dynamic collapse during restful breathing<br>12 mo: | 7 wk: PEEP maintained at 6 cm $H_2O$<br>8 wk: TBM suspected; PEEP increased to 10 cm $H_2O$<br>2 mo: Cardio-respiratory arrest necessitating chest compressions with recovery<br>3 mo: Severe cardio-respiratory episodes requiring major intervention began<br>6 mo: Moderate/severe TBM confirmed (complete loss of airway lumen with coughing/heavy breathing)<br>12 mo: | 1 mo: PIP (30 cm $H_2O$); PEEP (6 cm water)<br>3 mo 10 d: Cardio-respiratory arrest<br>3 mo, 14 d: Asfotase alfa dose increased to 15 mg/kg/wk; improvement seen within 2 wk and patient placed back into conventional ventilation<br>5 mo: Significant TBM identified; PEEP (12 cm $H_2O$)<br>8 mo: Significant improvement in respiratory function; PEEP (9 cm $H_2O$)<br>11 mo: Complete resolution of TBM; PIP (10 cm $H_2O$); PEEP (5 cm water)<br>12-22 mo: CPAP ventilation (with decreasing frequency); PEEP (4-5 cm $H_2O$) |

TABLE 2-continued

Overview of treatment and patient outcomes during.

| | Patient 1 | Patient 2 | Patient 3 | Patient 4 |
|---|---|---|---|---|
| | | Significant improvement to mild TBM; respiratory arrest resolved; lorazepam discontinued 13 mo: Discharged to home | Improvement to moderate TBM; severe respiratory episodes resolved 15 mo: Discharged to home | 23 mo: Discharged to home; CPAP 1 night/wk; PEEP (5 cm $H_2O$) |
| Current status | 15 mo: Complete clinical resolution of TBM and breathing room air | 17 mo: Normal appearing lower airways, but TBM only when coughing or bearing down 27 mo: Remained on ventilator; respiratory issues | 18 mo: Significant TBM remained 23 mo: Tracheostomy in situ with ventilator support | 2 y: Complete clinical resolution of TBM, breathing room air |

Example 2. TBM Patient 1

Patient 1 was a term male infant born to non-consanguineous parents (birth weight of 2,890 g). Immediately after birth, the patient presented poor feeding, significant hypotonia, and respiratory distress. Antenatal scans had shown shortening of long bones. He required CPAP ventilation on the first day after birth for respiratory distress. He received intravenous (IV) antibiotics (ampicillin and gentamicin) for 5 days because his mother was Group B *Streptococcus* positive. A skeletal survey of the patient at nine days old revealed skeletal manifestations of HPP with severe rickets and shortened long bones of the upper and lower limbs with bony spurs at the ends. There was absence of an ossification center in the patient's skull bones and the short bones of the patient's hands and feet. His biochemistry after birth was also suggestive of HPP, with elevated serum calcium of 3.04 mmol/L relative to the reference range of 2.25-2.74 mmol/L, and with undetectably low serum alkaline phosphatase (ALP) activity.

Patient 1 was transferred to a tertiary hospital and enrolled in the ENB-010-10 clinical trial at four weeks old. Consistent with the diagnosis of HPP, his pyridoxal 5'-phosphate (PLP) and inorganic pyrophosphate levels (PPi) were elevated prior to treatment. The PLP concentration was 4,740 ng/mL in comparison to the reference range of 11.8 ng/mL to 68.3 ng/mL, and the PPi concentration was 9.47 µM in comparison to the reference range of 1.33 µM to 5.7 µM.

Treatment of patient 1 with asfotase alfa at a dose of 2 mg/kg (6 mg/kg/week) commenced at one month and one day old. The patient was intubated and ventilated for general anaesthesia, and a central venous catheter was inserted for venous access. The patient could not be weaned off the ventilator as his respiratory function progressively worsened. He continued to have episodes of desaturations requiring an increase in PEEP from 5 cm to 8 cm $H_2O$.

A direct laryngotracheobronchoscopy (DLTB) performed at two months old (one month after commencing asfotase alfa) revealed severe laryngotracheobronchomalacia, which required PEEP of 12 cm $H_2O$ to keep the airways patent. The dose of asfotase alfa was then increased to 3 mg/kg/dose (9 mg/kg/week). The patient's respiratory function progressively improved with a reduction in ventilator pressures to PEEP of 6 cm $H_2O$. A flexible DLTB performed at nine months of age (eight months after commencing asfotase alfa) showed normal patency of the larynx, trachea, and left main bronchus with residual left bronchomalacia requiring PEEP of 6 cm $H_2O$ to keep the airways patent.

DLTB was repeated under anaesthesia at 12 months of age, which revealed resolution of laryngotracheobronchomalacia with mild left bronchomalacia. The patient was changed from PEEP to CPAP. His respiratory function progressively improved, and he was self-ventilating in room air with complete clinical resolution of the laryngotracheobronchomalacia by 15 months of age. Genetic analysis revealed that the patient was positive for an autosomal recessive mutation in the ALPL gene, which was found to be secondary to uniparental disomy (see Hancarova et al. Bone 81:765-6, 2015, hereby incorporated by reference in its entirety). The timeline of key events for patient 1 is shown in Table 3.

TABLE 3

Timeline of key events for TBM patient 1

| Age | Event |
|---|---|
| Pre-birth | Antenatal scans showed shortening of long bones |
| 0 | Poor feeding, significant hypotonia and respiratory distress. CPAP required at birth. |
| 9 day | Skeletal radiographs revealed characteristics of HPP including severe rickets; long bones of upper and lower limbs were short, |

TABLE 3-continued

Timeline of key events for TBM patient 1

| Age | Event |
|---|---|
| | with bony spurs at their ends; and absence of ossification center of skull bones and of short bones of hand and feet. |
| 1 month | Transferred to trial center. On CPAP with PEEP of 5 cm $H_2O$. |
| 1 month 1 day | First dose of asfotase alfa administered at 2 mg/kg (6 mg/kg/week). |
| 1 month 2 days | Central venous line insertion and change from CPAP to intermittent positive pressure ventilation (IPPV) or PEEP. |
| 1 month 5 days | PEEP of 10 cm $H_2O$. |
| 1 month 8 days | Tracheostomy for long term ventilation. |
| 2 months 3 days | Diagnosed with laryngotracheobronchomalacia. PEEP increased to 12 cm $H_2O$. |
| 2 months 24 days | Dose of asfotase alfa increased to 3 mg/kg (9 mg/kg/week) due to insufficient skeletal mineralisation. |
| 3 months | Discharged to hospital. |
| 9 months | DLTB performed. Resolution of tracheobronchomalacia with residual malacia of left bronchus. PEEP reduced to 6 cm $H_2O$. |
| 12 months | DLTB under anaesthesia. Significant improvement with mild left bronchomalacia. Weaned to CPAP with PEEP of 5 cm $H_2O$. |
| 15 months | Complete clinical resolution of TBM, and breathing room air. |

Example 3. TBM Patient 2

Figure 2B:

Patient 2 was a male infant born by spontaneous vaginal delivery at 37 weeks and 5 days of gestation to non-consanguineous parents (birth weight of 3,460 g) with Apgar scores were 2 at 1 and 5 minutes and 5 at 10 minutes. The patient was intubated and placed on a ventilator. Radiographs at one day of age revealed that the patient had remarkably diminished ossification of the skull with almost no cranial calcification. He also had diminished ossification and height of vertebral bodies and absent ossification of the humeral, radial, and ulnar metaphyses with marked metaphyseal irregularity, fragmentation, and fraying. The patient's chest was small, and the patient's bones were abnormal with absent ossification of medial ribs and *gracile* appearance of the ribs (FIG. 2A). His PLP (vitamin Bs) level was >2000 ng/mL. Symptoms of HPP in the patient's airways were also evident at 16 days of age in chest radiographs (FIG. 2B). The patient was transferred to a tertiary care children's hospital at 27 days of age and enrolled in a clinical trial. His ALP was 14 U/L. He required a PEEP of 8 cm $H_2O$.

Treatment with asfotase alfa was initiated at 5 weeks of age at a dose of 1 mg/kg six times per week, during which the patient required PEEP of 8 cm $H_2O$. A tracheostomy was performed at 6 weeks of age. The patient required constant ventilator support with a rate initially maintained at 40 bpm. He had significant chest compliance and was maintained on high PEEP up to 12 cm $H_2O$.

Gastrostomy was performed at 4 months of age. The need for continuous ventilator support and events of respiratory and cardiac arrest led to microlaryngobronchoscopy (MLB) and flexible bronchoscopy being performed at 5 months of age. MLB showed normal supraglottis, a type II laryngeal cleft, a normal appearing glottis, and Grade III stenosis of subglottis. Flexible bronchoscopy showed normal bronchial branching pattern, the subglottic space was significantly narrowed, severe cervical tracheomalacia, mild suprastomal tracheal collapse, and mild dynamic bronchial collapse during restful breathing, which was predicted to be more severe during agitation or heavy breathing. The patient experienced cardiac arrest at four and six months of age.

Figure 2C:
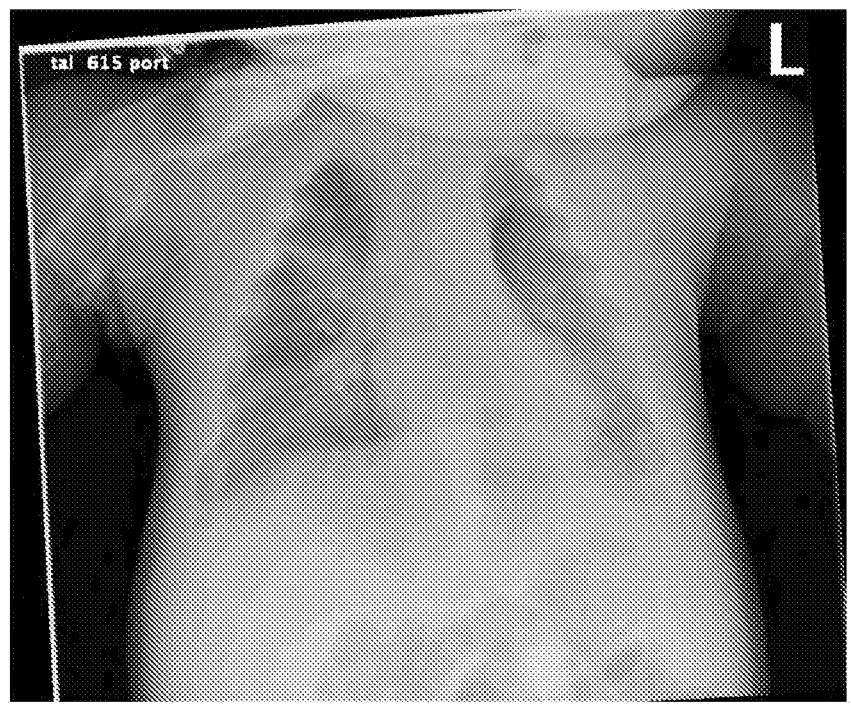
Figure 2D:
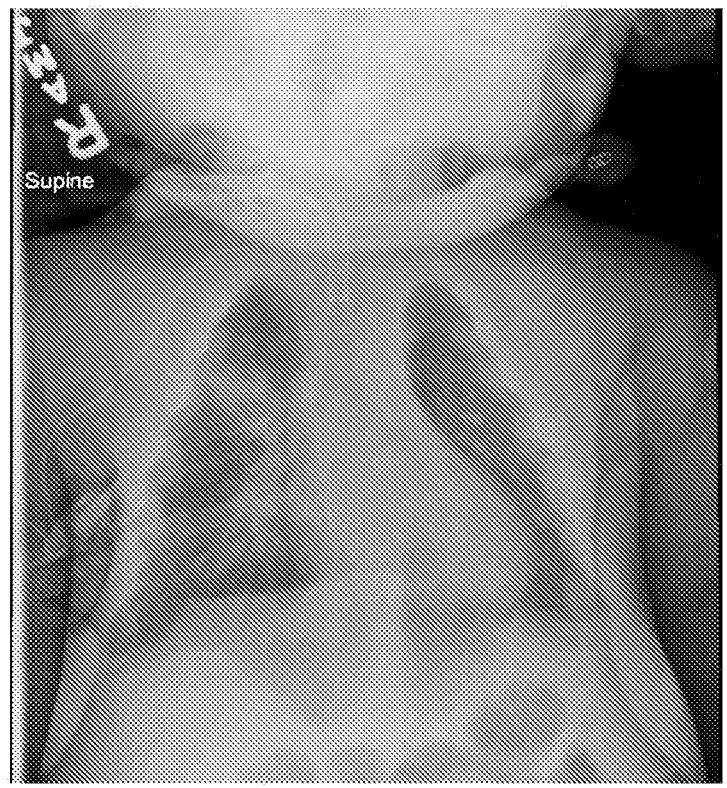

The dose of asfotase alfa administered was increased to 1.3 mg/kg (7.8 mg/kg/week) at 6 months of age. The dose of asfotase alfa was then changed to 2.5 mg/kg (7.5 mg/kg/week) at 9 months of age. Following treatment with asfotase alfa, improvements in HPP were visible in chest radiographs of the patient at 9 months and 12 months of age (FIGS. 2C-2D). The patient's TBM improved with mild dynamic collapse during restful breathing at 10 months of age. Bronchoscopy showed significant improvement with mild TBM at 12 months of age. The episodes of cardio-respiratory arrest resolved, and lorazepam was able to be weaned and then discontinued. Transferral to a tertiary care center occurred at 13 months of age, and the patient subsequently was discharged to home. The patient remained on a ventilator and has experienced respiratory issues with viral infections and hospital readmission.

The lower airways appeared normal at 17 months of age, with no appreciable dynamic collapse during breathing at rest; however, TBM manifested only when the patient was coughing or bearing down.

Genetic analysis of the ALPL gene revealed the patient to be a compound heterozygote with the following mutations: c.668 G>A and c.1171 C>T. The timeline of key events is shown in Table 4.

TABLE 4

Timeline of key events for TBM patient 2

| Age | Event |
|---|---|
| 0 | Intubated and placed on ventilator at birth for respiratory distress. |
| 1 day | Chest radiographs revealed characteristics of HPP including diminished ossification of skull; almost no cranial calcification; diminished ossification and height of vertebral bodies; absent ossification of humeral, radial, and ulnar metaphyses; marked |

TABLE 4-continued

Timeline of key events for TBM patient 2

| Age | Event |
|---|---|
| | metaphyseal irregularity, fragmentation, and fraying; small chest; abnormal bones; absent ossification of medial ribs; and gracile appearance of ribs (FIG. 2A). |
| 16 days | Chest radiographs show progression of HPP (FIG. 2B). |
| 27 days | Transferred to study center hospital. |
| 5 weeks | Started treatment with asfotase alfa of 1 mg/kg (6 mg/kg/week). PEEP of 8 cm $H_2O$ required. |
| 6 weeks | Tracheostomy. |
| 3 months | Respiratory arrest, required positive pressure ventilation, and reattached to ventilator. |
| 4 months | Gastrostomy. Intermittent oxygen desaturations not related to tracheal secretions. Treated with lorazepam and morphine for sedation. Episodes continued and responded to positive pressure ventilation. Cardio-respiratory arrest. |
| 5 months | Laryngotracheoscopy and bronchoscopy revealed severe cervical tracheomalacia. |
| 6 months | Cardio-respiratory arrest. Dose of asfotase alfa increased to 1.3 mg/kg (7.8 mg/kg/week). |
| 9 months | Dose of asfotase alfa changed to 2.5 mg/kg (7.5 mg/kg/week). Improvement in HPP as evidenced by radiographs (FIG. 2C). |
| 10 months | TBM improved with mild dynamic collapse during restful breathing. |
| 12 months | Significant improvement with mild TBM. Continued improvements in HPP as evidenced by radiographs (FIG. 2D). |
| 13 months | Patient transferred to a tertiary care center and subsequently discharged to home. |
| 17 months | Normal appearing lower airways, TBM evidenced only when the patient was coughing or bearing down, hospital readmission only sporadic. TBM improved in Patient 2; the need for ventilator support persisted, although the patient is weaning from PEEP and has brief ventilator-free periods during the day. |

Example 4. TBM Patient 3

Patient 3 was a female infant born to non-consanguineous parents. Her birth weight was 3.06 kg, length 45 cm, and head circumference 32 cm. She was delivered by a planned repeat caesarean section after spontaneous rupture of membranes. An abnormal fetal ultrasound was suggestive of a skeletal dysplasia, either HPP or osteogenesis imperfecta. A fetal echocardiogram was normal. Her Apgar scores were 6 at 1 minute, 7 at 5 minutes, and 8 at 10 minutes.

The patient initially required positive pressure ventilation (bagging) for the first 5 minutes, then intermittently for the next 5 minutes. She was intubated and placed on a ventilator. Initial examination showed very large anterior fontanelle, cranial moulding, small chest with subcostal retractions, and short deformed extremities with bowing (equinovarus). Her feet were angulated and clubbed with dimpling below knees. She was transferred to a tertiary care children's hospital for diagnosis and management. Radiographs revealed severely decreased mineralization, diffuse osteopenia, poorly ossified ribs, irregularity of the right proximal humerus consistent with fracture and atelectasis, and bilateral humeral fractures. Renal ultrasound at one day of age was normal; however, there were focal areas of cortical echogenicity in both kidneys consistent with nephrocalcinosis at one month of age. Ionized calcium was 1.31 mmol/L and phosphorus was 6.8 mmol/L at eight days of age. Ventilator settings had a PEEP of 6 cm $H_2O$ and a respirator rate of 20 bpm. The patient was transferred to the study center primary care hospital. Her ALP level was 18 U/L at five weeks. She required assisted ventilation and was treated with lorazepam (0.05 mg/kg) every 6 hours for agitation.

The patient had a tracheostomy at seven weeks of age. Bronchoscopy was also performed and revealed profound dynamic collapse of the trachea and bronchi during coughing or heavy breathing, even while intubated and receiving positive pressure. There was moderate collapse of the posterior tracheal wall with very light, intermittent suction, which was considered to be most likely due to a lack of outward elastic chest wall recoil. PEEP was maintained at 6 cm $H_2O$. The patient had a poor result at eight weeks of age on the non-invasive partial carbon dioxide rebreathing system (NICO) due to excessive chest compliance, lack of elastic recoil, and severe airway malacia. It was recommended to increase PEEP to 10 cm $H_2O$.

The patient was enrolled in a clinical trial at 7 weeks and 4 days of age to receive 1 mg/kg (6 mg/kg/week) of asfotase alfa. She had a respiratory arrest at two months of age with a drop in heart rate and oxygen desaturation, which necessitated chest compressions with recovery. The patient underwent microlaryngoscopy, bronchoscopy, and flexible tracheoscopy at 2.5 months of age. Significant findings were narrowed subglottis with lateral shelves, dynamic collapse, and moderate to severe tracheomalacia.

The patient had gastrostomy at three months of age. She was also noted to have respiratory episodes with severe oxygen desaturations requiring increased positive pressure ventilations (bagging). One episode was associated with a drop in heart rate necessitating chest compressions. Respiratory failure persisted and $CO_2$ levels remained elevated. Treatment with methadone was initiated to address sedation and pain issues.

Severe respiratory arrests requiring major intervention occurred on an almost weekly basis. Treatment with lorazepam was initiated along with methadone at four months of age. Bronchoscopy at five months of age showed profound bronchomalacia with complete loss of the airway lumen with coughing or heavy breathing. Methadone was weaned at six months of age. The patient also received midazolam as needed for agitation.

The severe cardio-respiratory episodes decreased in frequency. Flexible bronchoscopy at 12 months of age revealed moderate tracheobronchomalacia, which appeared to improve from her previous evaluation (six months), although still significant. The severe cardio-respiratory episodes resolved at 12 months of age. The patient was transferred to a primary care hospital at 15 months of age and was subsequently able to be discharged to home care.

Flexible bronchoscopy revealed significant TBM at 18 months of age. The severity of the tracheomalacia was difficult to assess as the long custom tracheostomy tube was very well positioned in the distal trachea.

Genetic analysis of the ALPL gene revealed the patient was a compound heterozygote with the following mutations: c.876_872delAGGGGACinsT and c.650T>C(p.V217A). The timeline of key events for patient 3 is shown in Table 5.

TABLE 5

Timeline of key events for TBM patient 3

| Age | Event |
| --- | --- |
| Pre-birth | Fetal ultrasound suggestive of HPP or osteogenesis imperfecta. |
| 0 | Intubated and placed on ventilator for respiratory distress at birth. Transferred to tertiary care children's hospital. |
| 1 day | Renal ultrasound normal. |
| 4 weeks | Renal ultrasound consistent with nephrocalcinosis. |
| 5 weeks | Patient transferred to study center primary care hospital. |
| 7 weeks | Tracheostomy. |
| 7 weeks 4 days | Enrolled in clinical trial, receiving asfotase alfa at 1 mg/kg (6 mg/kg/week). |
| 3 months | Gastrostomy. Respiratory episodes with severe oxygen desaturation requiring bagging. |
| 4 months | Lorazepam and methadone initiated. |
| 5 months | Bronchomalacia with complete loss of airway lumen identified on bronchoscopy. |
| 6 months | Methadone weaned. Midazolam as needed for agitation. |
| 12 months | Moderate TBM with improvements from 6 months. Severe respiratory episodes resolved. |
| 15 months | Transferred to primary care hospital and subsequently discharged to home care. |
| 18 months | While significant TBM remained, patient remained at home without additional cardio-respiratory episodes. |

Example 5. TBM Patient 4

Patient 4 was a 34-week preterm female infant born by normal vaginal delivery following premature rupture of membranes to consanguineous parents (birth weight was 1.69 kg). Immediately after birth, she was floppy with marked chest recessions. The patient required immediate intubation and ventilation to support breathing. Respiratory distress syndrome was suspected and surfactant therapy was administered. Despite low ventilator requirements, she continued to have significant respiratory distress and ventilation was continued.

The patient was found to have dysmorphic features with short limbs, craniotabes, and significant hypotonia. She was discussed with the tertiary metabolic bone disease team because she had hypercalcaemia with undetectably low ALP activity levels. Her skeletal survey revealed characteristic features of HPP. She was transferred to a tertiary neonatal unit for further management with asfotase alfa, under a compassionate use program. Her biochemistry results improved within seven days of commencing asfotase alfa, with a reduction in serum calcium levels. She continued to have increased ventilator requirements with significant episodes of bradycardia and desaturations, which required an increase in ventilator settings to peak inspiratory pressure (PIP) of 30 cm $H_2O$ and PEEP of 6 cm $H_2O$. Despite adequate ventilation, she continued to have episodes of desaturations and bradycardia, which culminated in an acute deterioration at two months and nine days of age with profound desaturations, bradycardia requiring chest compression, and inotropes for cardiac arrest. Subsequently, the patient required high frequency oscillatory ventilation, nitric oxide, 100% oxygen requirement, and inotropes for support of cardiac function. Concerns that she might not survive the acute episode led to discussion of withdrawal of cardio-pulmonary-resuscitation with the parents.

Following discussion with a clinical research team, the dose of asfotase alfa was increased to 5 mg/kg three times a week (15 mg/kg/week) at 3 months and 13 days of age. Within 2 weeks of treatment with 15 mg/kg/week of asfotase alfa, she showed improvement and was able to receive conventional ventilation. However, she continued to have episodes of bradycardia and desaturations and a thorough review by the ENT and respiratory team was planned. A DLTB performed at 5 months of age demonstrated significant laryngotracheobronchomalacia, which required PEEP of 12 cm $H_2O$ to keep the airways patent. Her respiratory function significantly improved with increase in PEEP and by 8 months of age, her PEEP was reduced to 9 cm $H_2O$.

A second DLTB was performed at 11 months of age, which showed complete resolution of laryngotracheobronchomalacia with opening pressure reduced to 4 cm $H_2O$. Her ventilator pressures were then weaned to PIP of 10 cm $H_2O$ and PEEP of 5 cm $H_2O$. Intermittent CPAP ventilation was introduced by 12 months of age with PEEP of 4 to 5 cm of water. By 16 months of age, she was self-ventilating in room air for 12 hours of the day. She was discharged home at 23 months of age on CPAP for 1 night a week. Her ventilation was completely discontinued at two years of age.

Genetic analysis showed a mutation in the ALPL gene, homozygous for C.1336G7A (PA446T) mutation, with both parents' carriers for the mutation. The timeline of key events s shown in Table 6.

TABLE 6

Timeline of key events for TBM patient 4

| Age | Event |
|---|---|
| 0 | Intubated and ventilated at birth. |
| 3 days | Skeletal survey revealed characteristics of HPP including dysmorphic features (short limbs), craniotabes, and significant hypotonia. |
| 5 days | HPP confirmed by biochemistry and skeletal survey images. |
| 8 days | Discussed with clinical research team for compassionate use. |
| 1 month | Transferred to neonatal unit. |
| 1 months 15 days | Tracheostomy insertion for long-term ventilation. |
| 2 months 13 days | Discharge from neonatal unit to paediatric intensive care unit. Pressures of PIP of 30 cm $H_2O$ and PEEP of 6 cm $H_2O$. |
| 3 months 10 days | Cardiac arrest requiring high frequency ventilation. |
| 3 months 14 days | Increased dose to 5 mg/kg/dose (15 mg/kg/week). Indications of increased ventilator requirements. |
| 5 months | DLTB and pressures increased to PEEP of 12 cm $H_2O$. |
| 9 months | Transferred to high dependency unit (HDU). PEEP of 9 cm $H_2O$. |
| 9.5 months | Transferred from HDU to long term ventilation unit. |
| 10 months | PIP of 13 cm and PEEP of 8 cm $H_2O$. |
| 11 months | DLTB improved PIP of 10 cm and PEEP of 5 cm $H_2O$. |
| 13 months | CPAP mode of ventilation. |
| 15 months | Off CPAP for 6 hours each day. |
| 16 months | CPAP only at night. |
| 22 months | CPAP only 2 nights a week. Pressure of 5 cm $H_2O$. |
| 23 months | Discharged home on CPAP ventilation for 1 night per week. PEEP of 5 cm $H_2O$. |
| 2 years | Complete clinical resolution of TBM, and breathing room air. |

Example 6. Sustained Improvements in Respiratory Function in Infants and Children Treated with Asfotase Alfa An open-label, multinational study was conducted to assess the efficacy and safety of asfotase alfa in a large cohort of patients with perinatal-onset HPP or infantile-onset HPP over approximately 168 weeks of treatment. Participants included 59 patients of five years of age or younger (27 male and 32 female patients) with first signs and symptoms of HPP prior to six months of age. These infants and children with perinatal-onset HPP or infantile-onset HPP received 6 to 9 mg/kg/week of asfotase alfa subcutaneously either as a dosage regimen of 1 mg/kg six times per week or 2 to 3 mg/kg three times per week.

Treatment of these infants and children having perinatal-onset HPP or infantile-onset HPP for three years or more with asfotase alfa resulted in significantly improved respiratory status, as indicated by reduced use of ventilation or supplemental oxygen. Of 19 HPP patients that required baseline respiratory support, this respiratory support was eliminated or reduced over the course of treatment for 11 patients (58%). Of the eight patients whose respiratory support was not reduced, five were on supplemental oxygen and three were on non-invasive ventilator support. Of the 40 patients who were free of baseline respiratory support, most patients (35 of 40; 88%) remained so throughout the study. A total of five patients developed the need for respiratory support after baseline, and two of these patients were subsequently weaned off support, while one patient required invasive support until the last assessment. A total of two patients required ventilator support until their deaths from HPP; however, their TBM status was unknown. These patients still responded to asfotase alfa treatment, as evidenced by improved respiratory status (e.g., reduced use of ventilation or supplemental oxygen) and improvements in skeletal manifestations of HPP.

These results demonstrate that improvements in respiratory status of infants and children with perinatal-onset HPP, juvenile-onset, or infantile-onset HPP due to treatment with asfotase alfa were sustained over an extended treatment period (e.g., three or more years).

Example 7. Respiratory Status of Patients with an Inferred Post-Diagnosis of Tracheobronchomalacia The following example provides information regarding the respiratory status of patients enrolled in a treatment study with STRENSIQ with an inferred post-diagnosis of TBM upon review of ventilator pressures recorded at the time of mechanical ventilation.

Study Design

The study was a multicenter, open-label, multinational study of the safety, efficacy, and pharmacokinetics (PK) of asfotase alfa (STRENSIQ®) in infants and children up to and including 5 years of age with perinatal- or infantile-onset HPP. Perinatal- and infantile-onset HPP was defined as onset of first signs/symptoms from in utero to before 6 months of age.

The study included patients with a documented diagnosis of HPP with onset of symptoms prior to 6 months of age and age years at study entry. This interim analysis includes 59 patients enrolled at 19 sites. Patients received a total of 6 mg/kg/week of asfotase alfa administered by subcutaneous (SC) injection, either as 1 mg/kg asfotase alfa 6 times per week or 2 mg/kg asfotase alfa 3 times per week per investigator discretion. Dose adjustments could be made for changes in weight and/or to improve safety and/or efficacy.

Baseline

There were 3 of 59 patients assessed in the interim analysis as presenting with TBM in the study (patients 11-13). Additionally, there were a total of 10 of 59 patients (patients 1-10) with an inferred post-diagnosis of TBM upon review of ventilator pressures recorded at the time of mechanical ventilation.

All 13 patients (7 male, 6 female) ranged in age from 0.1 weeks to 269.9 weeks old, and all displayed an abnormally shaped chest. At baseline, patient 1 required no respiratory support, patients 2-5, and 12 required endotracheal mechanical ventilation, patient 6 required supplemental oxygen, patients 7-10, and 13 required mechanical ventilation by tracheostomy, and patient 11 required continuous positive airway pressure (CPAP).\

Results

Patient 1 did not use respiratory support at study entry, but did require intermittent support (oxygen via facemask, bilevel or biphasic positive airway pressure (Bi PAP), and continuous positive airway pressure (CPAP) due to respiratory distress shortly after the 12 weeks and up to week 26. Inspiratory pressure and expiratory pressure during BiPAP was 18 and 8 cm $H_2O$, respectively. She was free of respiratory support from week 36 through week 216.

Patient 2 required continuous mechanical ventilation via endotracheal tube for respiratory support from study entry until week 24, when he was weaned from the ventilator and placed on supplemental 02 via nasal prongs. By week 36, he was free of respiratory support and remained free of support through week 192. At baseline, the mechanical ventilation inspiratory pressure was 0.35 cm $H_2O$ and expiratory pressure was 10 cm $H_2O$. At week 3, mechanical ventilation inspiratory pressure was 18 cm $H_2O$ and expiratory pressure was 13 cm $H_2O$. At week 6, mechanical ventilation inspiratory pressure was 33 cm $H_2O$ and expiratory pressure was 12 cm $H_2O$. At week 12, mechanical ventilation inspiratory pressure was 24 cm $H_2O$ and expiratory pressure was 7 cm $H_2O$.

Patient 3 required intubation at birth, with continuous mechanical ventilation respiratory support at baseline and throughout the time period evaluated in this study. The endotracheal tube was exchanged with a tracheostomy at week 24, which remained in place at the patient's last recorded visit at week 60. The patient died after experiencing acute respiratory failure on several occasions, with a background of atelectasis and pulmonary hypertension. Inspiratory pressure/expiratory pressure at baseline and weeks 3, 6, 12, 24, 36, 48, and 60 were —/10 cm $H_2O$, 29/12 cm $H_2O$, 24/9 cm $H_2O$, 26/10 cm $H_2O$, 32/11 cm $H_2O$, 40/10 cm $H_2O$, 29/12 cm $H_2O$, and 33/14 cm $H_2O$, respectively.

Patient 4 required mechanical ventilation via endotracheal tube/tracheostomy tube for respiratory support at baseline through week 48. At week 60, the patient was receiving continuous positive airway pressure (CPAP) and from week 72 through week 168 the patient was once again receiving mechanical ventilation via tracheostomy. Mechanical ventilation inspiratory pressure/expiratory pressure at baseline and weeks 3, 6, 12, 24, 36, 48, 60, 72, 96, 120, 144, and 168 were 26/7 cm $H_2O$, 30/7.5 cm $H_2O$, 30/9 cm $H_2O$, 29/8.7 cm $H_2O$, 27/6 cm $H_2O$, 13/4 cm $H_2O$, 14/5 cm $H_2O$, 5/5 cm $H_2O$ (week 60, as measured by CPAP), 24/5 cm $H_2O$, 12/5 cm $H_2O$, 12/5 cm $H_2O$, 13/5 cm $H_2O$, and 15/5 cm $H_2O$, respectively.

Patient 5 was placed on mechanical ventilation via endotracheal tube prior to starting the study; he was reported to have had multiple seizures and severe hypoxic episodes requiring increased oxygenation and positive pressure ventilation. The patient continued to require respiratory support at Baseline and at the last milestone visit at week 3, at which time the patient was discontinued from the study. After 2 doses of study drug this patient was withdrawn from the study by family/medical consensus when a brain magnetic resonance imaging (MRI) showed hypoxia induced lesions and encephalopathy (assessed as an unlikely related serious adverse event (SAE)). The patient died less than a week later of "respiratory failure and cerebral death", also assessed as unlikely related to the study drug and more likely due to the complications of the seizures. Mechanical ventilation inspiratory pressure/expiratory at baseline and at week 3 were 17/7 cm $H_2O$ and 22/7 cm $H_2O$, respectively.

Patient 6 required 24-hour supplementary oxygen at baseline due to difficulty breathing, and received mechanical ventilation (endotracheal or CPAP) from week 6 (just prior to a dose increase at week 7) through week 36 due to pneumonia, difficulty breathing, and/or respiratory worsening. At Week 48, the patient was reported to receive only intermittent supplementary oxygen; no respiratory support was received week 60 through week 96. Mechanical inspiratory pressure/expiratory pressure was 16/6 cm $H_2O$ at baseline. Endotracheal inspiratory pressure/expiratory pressure at week 6 was 16/6 cm $H_2O$. CPAP inspiratory pressure/expiratory pressure at weeks 12, 24, and 36 were 17/6 cm $H_2O$, 8/6 cm $H_2O$, and —/6, respectively.

Patient 7 was intubated prior to enrollment and removed from endotracheal mechanical ventilation support 1 day prior to the baseline visit. She was on nasal CPAP (non-invasive ventilation) for 1 day prior and at the start of study treatment. The patient used 24-hour oxygen support (30 L/Min) at baseline. Her need for oxygen support varied throughout the study, including BiPAP at week 6, manual resuscitation via bag mask at approximately week 9, mechanical ventilation via tracheostomy at week 12 and week 48 through week 72. Patient was on no ventilation support at week 96. Inspiratory pressure/expiratory pressure during ventilation support at baseline and weeks 3, 6, 12, 24, 36, and 48, were 31/7 cm $H_2O$, 25/7 cm $H_2O$, 18/10 cm $H_2O$, 21/8 cm $H_2O$, 25/5 cm $H_2O$, 25/5 cm $H_2O$, and 25/5 cm $H_2O$, respectively.

Patient 8 used mechanical ventilation with intermittent mandatory ventilation 10 times per minute at night via tracheostomy at baseline (inspiratory pressure 20.0 cm $H_2O$, expiratory pressure 5.0 cm $H_2O$). This level of mechanical ventilation continued until week 24. From Week 36 onward, no respiratory suppor" was noted.

Patient 9 required 24-hour mechanical ventilation via tracheostomy at baseline (inspiratory pressure 32.0 cm $H_2O$, expiratory pressure 6.0 cm $H_2O$, $FiO_2$ 35.0%, 35.0 L 02/min), which continued through week 72 with some improvement observed in lower inspiratory and expiratory pressures, ventilator rates, and $FiO_2$. Mechanical ventilation inspiratory/expiratory pressure at baseline and weeks 36, 48, and 60-72 were 32/6 cm $H_2O$, 26/6 cm $H_2O$, 22/5 cm $H_2O$, and 22/5 cm $H_2O$, respectively.

Patient 10 required 24-hour mechanical ventilation via tracheostomy at baseline. Inspiratory pressure of the mechanical ventilation was reduced over time, and from week 24 onward (through week 72) the patient required no respiratory support. Mechanical ventilation inspiratory/expiratory pressure at baseline and weeks 3-6 and 12 were 25/-cm $H_2O$, 17/-cm $H_2O$, and 11/-cm $H_2O$, respectively.

Patient 11 was receiving ventilation via CPAP ($FiO_2$ 30%, 24 hours a day) at baseline. At weeks 3, 6, and 12, the patient was receiving mechanical ventilation via tracheostomy. At week 24, the patient continued to receive ventilation support. CPAP inspiratory pressure/expiratory pressure was —/5 cm $H_2O$ at baseline. Mechanical ventilation inspiratory/expiratory pressure at weeks 3, 6, 12, and 24 were 18/10 cm $H_2O$, 20/12 cm $H_2O$, 1/3.4 cm $H_2O$, and 15/10 cm $H_2O$, respectively.

Patient 12 received 24-hour mechanical respiratory support (endotracheal and tracheostomy) during the study observation period from baseline to week 36, the last study visit prior to data cut-off. Mechanical ventilation inspiratory pressure/expiratory at baseline and weeks 3, 6, 12, 24, and 36 were 32/8 cm $H_2O$, 35/11 cm $H_2O$, 28/12 cm $H_2O$, 31/10 cm $H_2O$, 30/12 cm $H_2O$, and 34/13 cm $H_2O$, respectively.

Patient 13 was on mechanical ventilation (tracheostomy) from baseline to week 12. Mechanical ventilation inspiratory pressure/expiratory pressure at baseline, weeks 3-6, and week 12 were 24/6 cm $H_2O$, 30/8 cm $H_2O$, and 32/12 cm $H_2O$, respectively.

Of the 13 patients studied, the inspiratory/expiratory ratio decreased during the course of asfotase alfa treatment in 8 patients and increased in 3 patients. Insufficient data was collected for the remaining 2 patients. Inspiratory pressure increased in 6 of the 11 patients and expiratory pressure decreased or stayed the same in 7 of the patients, indicating an increase in lung capacity. Furthermore, 6 of the 13 patients required no ventilation support by the end of the testing period, which is indicative of a significant improvement in respiratory function following asfotase alfa treatment in patients with TBM.

OTHER EMBODIMENTS

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method of treating tracheobronchomalacia (TBM) in a human subject in need thereof, wherein the subject has having hypophosphatasia (HPP), comprising administering a soluble alkaline phosphatase (sALP) to the subject in a dosage regimen that provides greater than 6 mg/kg/week of the sALP to the subject, wherein the sALP comprises asfotase alfa (SEQ ID NO: 1) or an amino acid sequence having at least 95% sequence identity to the amino acid sequence of SEQ ID NO: 1, and wherein administration of the sALP results in an improvement in TBM in the subject.

2. The method of claim 1, wherein:
the sALP is administered twice a week, three times a week, four times a week, five times a week, six times a week, or seven times a week.

3. The method of claim 1, wherein the method improves one or more symptoms of TBM selected from the group consisting of cardio-respiratory arrest, tracheostomy, cardiac arrest, respiratory distress, sputum retention, wheezing, coughing, anoxic spells, cyanosis, bradycardia, tachyarrhythmia, spontaneous hyperextension of the neck, prolonged expiratory breathing phase, failure to thrive, sternal retractions, substernal retractions, intercostal retractions, intermittent dyspnea, continuous dyspnea, and recurrent bronchitis.

4. The method of claim 3, wherein at least one of:
a) the method improvement recurrent pneumonia; and
b) the method further comprising increasing the dosage of the sALP if the subject does not exhibit an improvement in one or more of the symptoms of TBM following administration of the sALP for a treatment period of at least two weeks, three weeks, one month, two months, three months, four months, five months, or six months.

5. The method of claim 4, wherein the subject exhibits an improvement in one or more of the symptoms of TBM after receiving an increased dosage of the sALP.

6. The method of claim 5, wherein the subject exhibits an improvement in one or more of the symptoms of TBM after a treatment period of about one week to about one year.

7. The method of claim 1, wherein at least one of:
a) the subject requires ventilator support prior to administration of the sALP, wherein the ventilator support is at least one of high frequency oscillatory ventilation, positive end-expiratory pressure (PEEP), continuous positive airway pressure (CPAP), bilevel or biphasic positive airway pressure (BiPAP), and intermittent positive pressure ventilation (IPPV); and
b) the subject exhibits decreased reliance on ventilator support, or no longer requires ventilator support, after administration of the sALP.

8. The method of claim 7, wherein at least one of:
a) the PEEP is from about 5 cm $H_2O$ to about 15 cm $H_2O$;
b) administration of the sALP results in a decrease in the PEEP required by the subject;
c) the CPAP is provided about once or twice per week;
d) administration of the sALP promotes a decrease in frequency and/or duration of CPAP; and
e) the method comprises a transition from PEEP to CPAP following administration of the sALP.

9. The method of claim 8, wherein:
the PEEP required by the subject decreases by about 1 cm $H_2O$ to about 10 cm $H_2O$ after administration of the sALP.

10. The method of claim 8, wherein the sALP is administered to the subject for about one to about ten months.

11. The method of claim 1, wherein:
the subject is an infant.

12. The method of claim 1, wherein at least one of:
a) administration of the sALP increases survival of the subject;
b) the method further comprises determining whether the subject has a mutation in the subject's tissue non-specific alkaline phosphatase (TNALP) gene; and
c) the method further comprises determining sALP activity in a serum sample and/or blood sample from the subject.

13. The method of claim 12, wherein the mutation in the TNALP gene is associated with HPP.

14. The method of claim 1, wherein the sALP is at least one of:
a) administered to the subject in a composition comprising a pharmaceutically acceptable excipient, carrier, or diluent;
b) administered on consecutive or alternating days;
c) physiologically active toward PEA, PPi, and PLP;
d) catalytically competent to improve skeletal mineralization in bone; and
e) the soluble extracellular domain of an ALP.

15. The method of claim 14, wherein the pharmaceutically acceptable excipient, carrier, or diluent comprises at least one of:
a) saline; and
b) sodium chloride and sodium phosphate.

16. The method of claim 15, wherein the pharmaceutically acceptable excipient, carrier, or diluent comprises 150 mM sodium chloride and 25 mM sodium phosphate.

17. The method of claim 14, wherein the composition is administered to the subject subcutaneously, intravenously, intramuscularly, intra-arterially, intrathecally, or intraperitoneally.

18. The method of claim 12, wherein the determining sALP activity comprises measuring the concentration of at least one of phosphoethanolamine (PEA), inorganic pyrophosphate (PPi), and pyridoxal 5'-phosphate (PLP) in the serum sample and/or blood sample.

19. The method of claim 1, wherein the sALP comprises an amino acid sequence having at least 96%, 97%, 98%, or 99% sequence identity to the amino acid sequence of SEQ ID NO: 1.

20. The method of claim 3, wherein:
a) one or more of the symptoms of TBM are present in the subject at birth; or
b) one or more of the symptoms of TBM develop in the subject subsequent to birth.

21. The method of claim 11, wherein:
a) one or more of the symptoms of HPP are present in the subject at birth; or
b) one or more of the symptoms of HPP develop in the subject subsequent to birth.

22. The method of claim 1, wherein the subject is diagnosed with TBM prior to administration of the sALP.

23. The method of claim 1, wherein the dosage regimen provides 6.5 mg/kg/week to about 25 mg/kg/week of the sALP to the subject.

24. The method of claim 23, wherein the dosage regimen comprises administering about 3 mg/kg of the sALP three times a week, about 2.5 mg/kg of the sALP three times a week, about 1.3 mg/kg of the sALP six times a week, or about 5 mg/kg of the sALP three times a week to the subject.

25. The method of claim 1, wherein the improvement in TBM is sustained throughout administration of the sALP for a treatment period of at least one year.

26. The method of claim 1, wherein prior to, concurrently with, or after administration of the sALP to the subject, the method further comprises performing a tracheostomy on the subject, performing a bronchoscopy on the subject, or administering respiratory support, wherein the respiratory support comprises at least one of high frequency oscillatory ventilation, positive end-expiratory pressure (PEEP), continuous positive airway pressure (CPAP), bilevel or biphasic positive airway pressure (BiPAP), and intermittent positive pressure ventilation (IPPV).

27. The method of claim 11, wherein administration of the sALP occurs about one to about six months after birth.

\* \* \* \* \*

UNITED STATES PATENT AND TRADEMARK OFFICE
CERTIFICATE OF CORRECTION

PATENT NO. : 11,116,821 B2
APPLICATION NO. : 16/325910
DATED : September 14, 2021
INVENTOR(S) : Saal It is certified that error appears in the above-identified patent and that said Letters Patent is hereby corrected as shown below:

In the Claims

Column 91, Claim 1, Lines 11-12, replace "wherein the subject has having hypophosphatasia (HPP)" with --wherein the subject has hypophosphatasia (HPP)--;
Claim 4, Line 36, replace "improvement" with --improves--;
Line 37, replace "comprising" with --comprises--.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 20

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220
```

-continued

```
Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
            245                 250                 255

Glu Leu Leu Thr Leu Asp Pro His Asn Val Asp Tyr Leu Leu Gly Leu
        260                 265                 270

Phe Glu Pro Gly Asp Met Gln Tyr Glu Leu Asn Arg Asn Asn Val Thr
    275                 280                 285

Asp Pro Ser Leu Ser Glu Met Val Val Ala Ile Gln Ile Leu Arg
290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
```

```
                        645                 650                 655
Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
            675                 680                 685

Val Phe Ser Cys Ser Val Met His Glu Ala Leu His Asn His Tyr Thr
            690                 695                 700

Gln Lys Ser Leu Ser Leu Ser Pro Gly Lys Asp Ile Asp Asp Asp Asp
705                 710                 715                 720

Asp Asp Asp Asp Asp Asp
                    725

<210> SEQ ID NO 2
<211> LENGTH: 524
<212> TYPE: PRT
<213> ORGANISM: Homo sapiens

<400> SEQUENCE: 2

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285
```

```
Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305             310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
130                 135                 140
```

-continued

Asn Glu Val Thr Ser Ile Leu Arg Trp Ala Lys Asp Ala Gly Lys Ser
145                 150                 155                 160

Val Gly Ile Val Thr Thr Arg Val Asn His Ala Thr Pro Ser Ala
            165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415
```

```
Asn Gly Pro Gly Tyr Lys Val Val Gly Gly Glu Arg Glu Asn Val Ser
            420                 425                 430

Met Val Asp Tyr Ala His Asn Tyr Gln Ala Gln Ser Ala Val Pro
            435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
                515                 520

<210> SEQ ID NO 5
<211> LENGTH: 524
<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65              70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
```

```
                260                 265                 270
Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 6
<211> LENGTH: 524
<212> TYPE: PRT
<213> ORGANISM: Homo sapiens

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110
```

```
Thr Ala Thr Ala Tyr Leu Cys Gly Val Lys Ala Asn Glu Gly Thr Val
            115                 120                 125
Gly Val Ser Ala Ala Thr Glu Arg Ser Arg Cys Asn Thr Thr Gln Gly
130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
            180                 185                 190
Pro Pro Glu Ala Leu Ser Gln Gly Cys Lys Asp Ile Ala Tyr Gln Leu
        195                 200                 205
Met His Asn Ile Arg Asp Ile Asp Val Ile Met Gly Gly Gly Arg Lys
    210                 215                 220
Tyr Met Tyr Pro Lys Asn Lys Thr Asp Val Glu Tyr Glu Ser Asp Glu
225                 230                 235                 240
Lys Ala Arg Gly Thr Arg Leu Asp Gly Leu Asp Leu Val Asp Thr Trp
                245                 250                 255
Lys Ser Phe Lys Pro Arg His Lys His Ser His Phe Ile Trp Asn Arg
            260                 265                 270
Thr Glu Leu Leu Thr Leu Asp Pro His Asn Val Asp Tyr Leu Leu Gly
        275                 280                 285
Leu Phe Glu Pro Gly Asp Met Gln Tyr Glu Leu Asn Arg Asn Asn Val
    290                 295                 300
Thr Asp Pro Ser Leu Ser Glu Met Val Val Ala Ile Gln Ile Leu
305                 310                 315                 320
Arg Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
            340                 345                 350
Val Glu Met Asp Arg Ala Ile Gly Gln Ala Gly Ser Leu Thr Ser Ser
        355                 360                 365
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ser Lys
    450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser Ala Gly Ser Leu Ala Ala Gly Pro Leu Leu
            500                 505                 510
Leu Ala Leu Ala Leu Tyr Pro Leu Ser Val Leu Phe
        515                 520
```

<210> SEQ ID NO 7
<211> LENGTH: 652
<212> TYPE: PRT
<213> ORGANISM: Macaca mulatta

<400> SEQUENCE: 7

Met Pro Thr Val Lys Thr Lys Gln Glu Ser His Ala Gly Ser Gly Ser
1               5                   10                  15

Gly Pro Arg Leu Ala Glu Arg Lys Gly Arg Val Gly Ala Ala Arg Arg
            20                  25                  30

Gln Ser Pro Arg Ala Pro Gly Gly Leu Pro Gly Pro Arg Ser Gly
        35                  40                  45

Pro Ala Ala Ala Phe Ile Arg Arg Gly Arg Trp Pro Gly Pro Arg
50                  55                  60

Cys Ala Pro Ala Thr Pro Arg Pro Arg Ser Arg Leu Cys Ala Pro Thr
65                  70                  75                  80

Arg Leu Cys Leu Asp Glu Pro Ser Ser Val Leu Cys Ala Gly Leu Glu
                85                  90                  95

His Gln Leu Thr Ser Asp His Cys Gln Pro Thr Pro Ser His Pro Arg
            100                 105                 110

Arg Ser His Leu Trp Ala Ser Gly Ile Lys Gln Val Leu Gly Cys Thr
        115                 120                 125

Met Ile Ser Pro Phe Leu Val Leu Ala Ile Gly Thr Cys Leu Thr Asn
130                 135                 140

Ser Leu Val Pro Glu Lys Glu Lys Asp Pro Lys Tyr Trp Arg Asp Gln
145                 150                 155                 160

Ala Gln Glu Thr Leu Lys Tyr Ala Leu Glu Leu Gln Lys Leu Asn Thr
                165                 170                 175

Asn Val Ala Lys Asn Val Ile Met Phe Leu Gly Asp Gly Met Gly Val
            180                 185                 190

Ser Thr Val Thr Ala Thr Arg Ile Leu Lys Gly Gln Leu His His Asn
        195                 200                 205

Pro Gly Glu Glu Thr Arg Leu Glu Met Asp Lys Phe Pro Phe Val Ala
210                 215                 220

Leu Ser Lys Thr Tyr Asn Thr Asn Ala Gln Val Pro Asp Ser Ala Gly
225                 230                 235                 240

Thr Ala Thr Ala Tyr Leu Cys Gly Val Lys Ala Asn Glu Gly Thr Val
                245                 250                 255

Gly Val Ser Ala Ala Thr Glu Arg Ser Arg Cys Asn Thr Thr Gln Gly
            260                 265                 270

Asn Glu Val Thr Ser Ile Leu Arg Trp Ala Lys Asp Ala Gly Lys Ser
        275                 280                 285

Val Gly Ile Val Thr Thr Thr Arg Val Asn His Ala Thr Pro Ser Ala
290                 295                 300

Ala Tyr Ala His Ser Ala Asp Arg Asp Trp Tyr Ser Asp Asn Glu Met
305                 310                 315                 320

Pro Pro Glu Ala Leu Ser Gln Gly Cys Lys Asp Ile Ala Tyr Gln Leu
                325                 330                 335

Val His Asn Ile Arg Asp Ile Asp Val Ile Met Gly Gly Gly Arg Lys
            340                 345                 350

Tyr Met Tyr Pro Lys Asn Lys Thr Asp Val Glu Tyr Glu Ile Asp Glu
        355                 360                 365

Lys Ala Arg Gly Thr Arg Leu Asp Gly Leu Asp Leu Val Asn Ile Trp
370                 375                 380

-continued

Lys Ser Phe Lys Pro Arg His Lys His Ser His Phe Ile Trp Asn Arg
385                 390                 395                 400

Thr Glu Leu Leu Thr Leu Asp Pro His Asn Val Asp Tyr Leu Leu Gly
            405                 410                 415

Leu Phe Glu Pro Gly Asp Met Glu Tyr Glu Leu Asn Arg Asn Asn Val
        420                 425                 430

Thr Asp Pro Ser Leu Ser Glu Met Val Val Ala Ile Gln Ile Leu
    435                 440                 445

Arg Lys Asn Pro Lys Gly Phe Leu Leu Val Glu Gly Arg Ile
450                 455                 460

Asp His Gly His His Glu Gly Lys Ala Lys Gln Ala Leu His Glu Ala
465                 470                 475                 480

Val Glu Met Asp Arg Ala Ile Gly Gln Ala Gly Ser Met Thr Ser Leu
            485                 490                 495

Glu Asp Thr Leu Thr Val Val Thr Ala Asp His Ser His Val Phe Thr
        500                 505                 510

Phe Gly Gly Tyr Thr Pro Arg Gly Asn Ser Ile Phe Gly Leu Ala Pro
    515                 520                 525

Met Leu Ser Asp Thr Asp Lys Lys Pro Phe Thr Ala Ile Leu Tyr Gly
530                 535                 540

Asn Gly Pro Gly Tyr Lys Val Val Gly Gly Glu Arg Glu Asn Val Ser
545                 550                 555                 560

Met Val Asp Tyr Ala His Asn Asn Tyr Gln Ala Ser Ala Val Pro
            565                 570                 575

Leu Arg His Glu Thr His Gly Gly Glu Asp Val Ala Val Phe Ser Lys
        580                 585                 590

Gly Pro Met Ala His Leu Leu His Gly Val His Glu Gln Asn Tyr Ile
    595                 600                 605

Pro His Val Met Ala Tyr Ala Ala Cys Ile Gly Ala Asn Leu Asp His
610                 615                 620

Cys Ala Pro Ala Ser Ser Ala Gly Ser Leu Ala Ala Gly Pro Leu Leu
625                 630                 635                 640

Leu Pro Leu Ala Leu Phe Pro Leu Ser Ile Leu Phe
            645                 650

<210> SEQ ID NO 8
<211> LENGTH: 524
<212> TYPE: PRT
<213> ORGANISM: Rattus norvegicus

<400> SEQUENCE: 8

Met Ile Leu Pro Phe Leu Val Leu Ala Ile Gly Pro Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Ile Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
        100                 105                 110

-continued

```
Thr Ala Thr Ala Tyr Leu Cys Gly Val Lys Ala Asn Glu Gly Thr Val
            115                 120                 125

Gly Val Ser Ala Ala Thr Glu Arg Thr Arg Cys Asn Thr Thr Gln Gly
        130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Arg Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Glu Ala Ile Gly Lys Ala Gly Thr Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Ser Ser Ala Ser Ser Pro Ser Gly Ala Leu Leu
            500                 505                 510

Leu Pro Leu Ala Leu Phe Pro Leu Arg Thr Leu Phe
        515                 520
```

<210> SEQ ID NO 9
<211> LENGTH: 502
<212> TYPE: PRT
<213> ORGANISM: Canis lupus familiaris

<400> SEQUENCE: 9

| | | | | | | | | | | | | | |
|---|---|---|---|---|---|---|---|---|---|---|---|---|---|
| Glu | Lys | Asp | Pro | Lys | Tyr | Trp | Arg | Asp | Gln | Ala | Gln | Gln | Thr | Leu | Lys |
| 1 | | | | 5 | | | | | 10 | | | | | 15 | |

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
                85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125

Leu Arg Trp Ala Lys Asp Ala Gly Lys Ser Val Gly Ile Val Thr Thr
    130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp
            180                 185                 190

Ile Glu Val Ile Met Gly Gly Gly Arg Lys Tyr Met Phe Pro Lys Asn
        195                 200                 205

Arg Thr Asp Val Glu Tyr Glu Met Asp Glu Lys Ser Thr Gly Ala Arg
    210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                245                 250                 255

Asp Pro Tyr Thr Val Asp Tyr Leu Leu Gly Leu Phe Asp Pro Gly Asp
            260                 265                 270

Met Gln Tyr Glu Leu Asn Arg Asn Asn Val Thr Asp Pro Ser Leu Ser
        275                 280                 285

Glu Met Val Glu Ile Ala Ile Lys Ile Leu Ser Lys Lys Pro Arg Gly
    290                 295                 300

Phe Phe Leu Leu Val Glu Gly Arg Ile Asp His Gly His His Glu
305                 310                 315                 320

Gly Lys Ala Lys Gln Ala Leu His Glu Ala Val Glu Met Asp Arg Ala
                325                 330                 335

Ile Gly Lys Ala Gly Val Met Thr Ser Leu Glu Asp Thr Leu Thr Val
            340                 345                 350

Val Thr Ala Asp His Ser His Val Phe Thr Phe Gly Gly Tyr Thr Pro
        355                 360                 365

Arg Gly Asn Ser Ile Phe Gly Leu Ala Pro Met Val Ser Asp Thr Asp
    370                 375                 380

```
Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                405                 410                 415

Asn Asn Tyr Gln Ala Gln Ser Ala Val Pro Leu Arg His Glu Thr His
            420                 425                 430

Gly Gly Glu Asp Val Ala Val Phe Ala Lys Gly Pro Met Ala His Leu
            435                 440                 445

Leu His Gly Val His Glu Gln Asn Tyr Ile Pro His Val Met Ala Tyr
        450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                485                 490                 495

Pro Val Gly Ile Leu Phe
            500

<210> SEQ ID NO 10
<211> LENGTH: 252
<212> TYPE: PRT
<213> ORGANISM: Sus scrofa

<400> SEQUENCE: 10

Ala Glu Leu Leu Ala Leu Asp Pro His Thr Val Asp Tyr Leu Leu Gly
1               5                   10                  15

Leu Phe Glu Pro Gly Asp Met Gln Tyr Glu Leu Asn Arg Asn Asn Val
            20                  25                  30

Thr Asp Pro Ser Leu Ser Glu Met Val Glu Met Ala Ile Arg Ile Leu
        35                  40                  45

Ile Lys Asn Pro Lys Gly Phe Phe Leu Leu Val Glu Gly Gly Arg Ile
    50                  55                  60

Asp His Gly His His Glu Gly Lys Ala Lys Gln Ala Leu His Glu Ala
65                  70                  75                  80

Val Glu Met Asp Arg Ala Ile Glu Gln Ala Gly Ser Met Thr Ser Val
                85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
        115                 120                 125

Met Val Ser Asp Thr Asp Lys Lys Pro Phe Thr Ala Ile Leu Tyr Gly
    130                 135                 140

Asn Gly Pro Gly Tyr Lys Val Val Gly Gly Glu Arg Glu Asn Val Ser
145                 150                 155                 160

Met Val Asp Tyr Ala His Asn Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
        195                 200                 205

Pro His Val Met Ala Tyr Ala Ala Cys Val Gly Ala Asn Arg Asp His
    210                 215                 220

Cys Ala Ser Ala Ser Ser Gly Ser Pro Ser Pro Gly Pro Leu Leu
225                 230                 235                 240

Leu Leu Leu Ala Leu Leu Pro Leu Gly Ile Leu Phe
```

<210> SEQ ID NO 11
<211> LENGTH: 524
<212> TYPE: PRT
<213> ORGANISM: Mus musculus

<400> SEQUENCE: 11

```
Met Ile Ser Pro Phe Leu Val Leu Ala Ile Gly Thr Cys Leu Thr Asn
 1               5                  10                  15

Ser Phe Val Pro Glu Lys Glu Arg Asp Pro Ser Tyr Trp Arg Gln Gln
                20                  25                  30

Ala Gln Glu Thr Leu Lys Asn Ala Leu Lys Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Lys Ala Gly Ala Met Thr Ser Gln
        355                 360                 365
```

-continued

```
Lys Asp Thr Leu Thr Val Val Thr Ala Asp His Ser His Val Phe Thr
370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
                405                 410                 415
Asn Gly Pro Gly Tyr Lys Val Val Asp Gly Glu Arg Glu Asn Val Ser
                420                 425                 430
Met Val Asp Tyr Ala His Asn Asn Tyr Gln Ala Gln Ser Ala Val Pro
                435                 440                 445
Leu Arg His Glu Thr His Gly Gly Glu Asp Val Ala Val Phe Ala Lys
450                 455                 460
Gly Pro Met Ala His Leu Leu His Gly Val His Glu Gln Asn Tyr Ile
465                 470                 475                 480
Pro His Val Met Ala Tyr Ala Ser Cys Ile Gly Ala Asn Leu Asp His
                485                 490                 495
Cys Ala Trp Ala Gly Ser Gly Ser Ala Pro Ser Pro Gly Ala Leu Leu
                500                 505                 510
Leu Pro Leu Ala Val Leu Ser Leu Arg Thr Leu Phe
515                 520
```

<210> SEQ ID NO 12
<211> LENGTH: 524
<212> TYPE: PRT
<213> ORGANISM: Bos taurus

<400> SEQUENCE: 12

```
Met Ile Ser Pro Phe Leu Leu Ala Ile Gly Thr Cys Phe Ala Ser
1               5                   10                  15
Ser Leu Val Pro Glu Lys Glu Lys Asp Pro Lys Tyr Trp Arg Asp Gln
                20                  25                  30
Ala Gln Gln Thr Leu Lys Asn Ala Leu Arg Leu Gln Thr Leu Asn Thr
            35                  40                  45
Asn Val Ala Lys Asn Val Ile Met Phe Leu Gly Asp Gly Met Gly Val
        50                  55                  60
Ser Thr Val Thr Ala Ala Arg Ile Leu Lys Gly Gln Leu His His Ser
65                  70                  75                  80
Pro Gly Glu Glu Thr Lys Leu Glu Met Asp Lys Phe Pro Tyr Val Ala
                85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
        115                 120                 125
Gly Val Ser Ala Ala Thr Gln Arg Ser Gln Cys Asn Thr Thr Gln Gly
    130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ser Tyr Ala His Ser Ala Asp Arg Asp Trp Tyr Ser Asp Asn Glu Met
            180                 185                 190
Pro Pro Glu Ala Leu Ser Gln Gly Cys Lys Asp Ile Ala Tyr Gln Leu
        195                 200                 205
Met His Asn Ile Lys Asp Ile Glu Val Ile Met Gly Gly Gly Arg Lys
    210                 215                 220
```

```
Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
            245                 250                 255

Lys Ser Phe Lys Pro Lys His Lys Ser His Tyr Val Trp Asn Arg
        260                 265                 270

Thr Asp Leu Leu Ala Leu Asp Pro His Ser Val Asp Tyr Leu Leu Gly
            275                 280                 285

Leu Phe Glu Pro Gly Asp Met Gln Tyr Glu Leu Asn Arg Asn Asn Ala
        290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
        450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
            500                 505                 510

Leu Leu Leu Ala Leu Leu Pro Leu Gly Ser Leu Phe
            515                 520

<210> SEQ ID NO 13
<211> LENGTH: 524
<212> TYPE: PRT
<213> ORGANISM: Bos taurus

<400> SEQUENCE: 13

Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
```

-continued

```
                65                  70                  75                  80
Pro Gly Glu Glu Thr Lys Leu Glu Met Asp Lys Phe Pro Tyr Val Ala
                        85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
                115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Lys Asp Ile Glu Val Ile Met Gly Gly Gly Arg Lys
                210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys Ser His Tyr Val Trp Asn Arg
                260                 265                 270

Thr Asp Leu Leu Ala Leu Asp Pro His Ser Val Asp Tyr Leu Leu Gly
            275                 280                 285

Leu Phe Glu Pro Gly Asp Met Gln Tyr Glu Leu Asn Arg Asn Asn Ala
            290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Gln Ala Ile Gly Gln Ala Gly Ala Met Thr Ser Val
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
            450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495
```

```
Cys Ala Ser Ala Ser Ser Ser Gly Ser Pro Ser Pro Gly Pro Leu Leu
                500                 505                 510

Leu Leu Leu Ala Leu Leu Pro Leu Gly Ser Leu Phe
        515                 520

<210> SEQ ID NO 14
<211> LENGTH: 124
<212> TYPE: PRT
<213> ORGANISM: Bos taurus

<400> SEQUENCE: 14

Asp Pro Lys Tyr Trp Arg Asp Gln Ala Gln Gln Thr Leu Lys Asn Ala
1               5                   10                  15

Leu Gly Leu Gln Lys Leu Asn Thr Lys Val Ala Lys Asn Val Ile Leu
            20                  25                  30

Phe Leu Gly Asp Gly Met Gly Val Ser Thr Val Thr Ala Ala Arg Ile
        35                  40                  45

Leu Lys Gly Gln Leu His His Asn Pro Gly Glu Glu Thr Arg Leu Glu
    50                  55                  60

Met Asp Lys Phe Pro Phe Val Ala Leu Ser Lys Thr Tyr Asn Thr Asn
65                  70                  75                  80

Ala Gln Val Pro Asp Ser Ala Gly Thr Ala Pro His Pro Val Arg Val
                85                  90                  95

Lys Ala Met Arg Ala Pro Trp Gly Glu Pro His Gln Arg Gln Cys Asn
            100                 105                 110

Thr Arg Arg Ala Thr Ser Thr His Leu Leu Ala Gly
        115                 120

<210> SEQ ID NO 15
<211> LENGTH: 524
<212> TYPE: PRT
<213> ORGANISM: Felis catus

<400> SEQUENCE: 15

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Lys Leu Asn Thr
        35                  40                  45

Asn Val Val Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Thr Gln Cys Asn Thr Thr Gln Gly
    130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175
```

```
Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Val Arg Asp Ile Glu Val Ile Met Gly Gly Gly Arg Lys
    210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
        275                 280                 285

Leu Phe Glu Pro Gly Asp Met Gln Tyr Glu Leu Asn Arg Asn Ser Thr
    290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Arg Ala Gly Ala Met Thr Ser Val
        355                 360                 365

Glu Asp Thr Leu Thr Ile Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
            500                 505                 510

Leu Leu Leu Ala Leu Pro Ser Leu Gly Ile Leu Phe
        515                 520

<210> SEQ ID NO 16
<211> LENGTH: 532
<212> TYPE: PRT
<213> ORGANISM: Homo sapiens

<400> SEQUENCE: 16

Met Gln Gly Pro Trp Val Leu Leu Leu Gly Leu Arg Leu Gln Leu
1               5                   10                  15

Ser Leu Gly Ile Ile Pro Val Glu Glu Glu Asn Pro Asp Phe Trp Asn
```

```
            20                  25                  30
Arg Gln Ala Ala Glu Ala Leu Gly Ala Ala Lys Lys Leu Gln Pro Ala
            35                  40                  45
Gln Thr Ala Ala Lys Asn Leu Ile Ile Phe Leu Gly Asp Gly Met Gly
        50                  55                  60
Val Ser Thr Val Thr Ala Ala Arg Ile Leu Lys Gly Gln Lys Lys Asp
65                  70                  75                  80
Lys Leu Gly Pro Glu Thr Phe Leu Ala Met Asp Arg Phe Pro Tyr Val
                85                  90                  95
Ala Leu Ser Lys Thr Tyr Ser Val Asp Lys His Val Pro Asp Ser Gly
            100                 105                 110
Ala Thr Ala Thr Ala Tyr Leu Cys Gly Val Lys Gly Asn Phe Gln Thr
            115                 120                 125
Ile Gly Leu Ser Ala Ala Arg Phe Asn Gln Cys Asn Thr Thr Arg
            130                 135                 140
Gly Asn Glu Val Ile Ser Val Met Asn Arg Ala Lys Lys Ala Gly Lys
145                 150                 155                 160
Ser Val Gly Val Val Thr Thr Thr Arg Val Gln His Ala Ser Pro Ala
                165                 170                 175
Gly Ala Tyr Ala His Thr Val Asn Arg Asn Trp Tyr Ser Asp Ala Asp
            180                 185                 190
Val Pro Ala Ser Ala Arg Gln Glu Gly Cys Gln Asp Ile Ala Thr Gln
            195                 200                 205
Leu Ile Ser Asn Met Asp Ile Asp Val Ile Leu Gly Gly Gly Arg Lys
            210                 215                 220
Tyr Met Phe Pro Met Gly Thr Pro Asp Pro Glu Tyr Pro Asp Asp Tyr
225                 230                 235                 240
Ser Gln Gly Gly Thr Arg Leu Asp Gly Lys Asn Leu Val Gln Glu Trp
                245                 250                 255
Leu Ala Lys His Gln Gly Ala Arg Tyr Val Trp Asn Arg Thr Glu Leu
            260                 265                 270
Leu Gln Ala Ser Leu Asp Pro Ser Val Thr His Leu Met Gly Leu Phe
            275                 280                 285
Glu Pro Gly Asp Met Lys Tyr Glu Ile His Arg Asp Ser Thr Leu Asp
            290                 295                 300
Pro Ser Leu Met Glu Met Thr Glu Ala Ala Leu Leu Leu Leu Ser Arg
305                 310                 315                 320
Asn Pro Arg Gly Phe Phe Leu Phe Val Glu Gly Gly Arg Ile Asp His
                325                 330                 335
Gly His His Glu Ser Arg Ala Tyr Arg Ala Leu Thr Glu Thr Ile Met
            340                 345                 350
Phe Asp Asp Ala Ile Glu Arg Ala Gly Gln Leu Thr Ser Glu Glu Asp
            355                 360                 365
Thr Leu Ser Leu Val Thr Ala Asp His Ser His Val Phe Ser Phe Gly
            370                 375                 380
Gly Tyr Pro Leu Arg Gly Ser Ser Ile Phe Gly Leu Ala Pro Gly Lys
385                 390                 395                 400
Ala Arg Asp Arg Lys Ala Tyr Thr Val Leu Leu Tyr Gly Asn Gly Pro
                405                 410                 415
Gly Tyr Val Leu Lys Asp Gly Ala Arg Pro Asp Val Thr Glu Ser Glu
            420                 425                 430
Ser Gly Ser Pro Glu Tyr Arg Gln Gln Ser Ala Val Pro Leu Asp Gly
            435                 440                 445
```

-continued

```
Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Gly Thr
            515                 520                 525

Ala Thr Ala Pro
        530

<210> SEQ ID NO 17
<211> LENGTH: 535
<212> TYPE: PRT
<213> ORGANISM: Homo sapiens

<400> SEQUENCE: 17

Met Leu Gly Pro Cys Met Leu Leu Leu Leu Leu Leu Gly Leu Arg
1               5                   10                  15

Leu Gln Leu Ser Leu Gly Ile Ile Pro Val Glu Glu Glu Asn Pro Asp
            20                  25                  30

Phe Trp Asn Arg Glu Ala Ala Glu Ala Leu Gly Ala Ala Lys Lys Leu
        35                  40                  45

Gln Pro Ala Gln Thr Ala Ala Lys Asn Leu Ile Ile Phe Leu Gly Asp
    50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
            100                 105                 110

Asp Ser Gly Ala Thr Ala Thr Ala Tyr Leu Cys Gly Val Lys Gly Asn
        115                 120                 125

Phe Gln Thr Ile Gly Leu Ser Ala Ala Ala Arg Phe Asn Gln Cys Asn
    130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
        195                 200                 205

Ala Thr Gln Leu Ile Ser Asn Met Asp Ile Asp Val Ile Leu Gly Gly
    210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
```

```
            275                 280                 285
Gly Leu Phe Glu Pro Gly Asp Met Lys Tyr Glu Ile His Arg Asp Ser
    290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
            340                 345                 350

Thr Ile Met Phe Asp Asp Ala Ile Glu Arg Ala Gly Gln Leu Thr Ser
        355                 360                 365

Glu Glu Asp Thr Leu Ser Leu Val Thr Ala Asp His Ser His Val Phe
    370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415

Asn Gly Pro Gly Tyr Val Leu Lys Asp Gly Ala Arg Pro Asp Val Thr
            420                 425                 430

Glu Ser Glu Ser Gly Ser Pro Glu Tyr Arg Gln Gln Ser Ala Val Pro
        435                 440                 445

Leu Asp Glu Glu Thr His Ala Gly Glu Asp Val Ala Val Phe Ala Arg
    450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
            500                 505                 510

Ser Val Val Pro Ala Leu Leu Pro Leu Leu Ala Gly Thr Leu Leu Leu
        515                 520                 525

Leu Glu Thr Ala Thr Ala Pro
    530                 535

<210> SEQ ID NO 18
<211> LENGTH: 532
<212> TYPE: PRT
<213> ORGANISM: Homo sapiens

<400> SEQUENCE: 18

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110
```

```
Ala Thr Ala Thr Ala Tyr Leu Cys Gly Val Lys Gly Asn Phe Gln Thr
            115                 120                 125
Ile Gly Leu Ser Ala Ala Arg Phe Asn Gln Cys Asn Thr Thr Arg
130                 135                 140
Gly Asn Glu Val Ile Ser Val Met Asn Arg Ala Lys Lys Ala Gly Lys
145                 150                 155                 160
Ser Val Gly Val Val Thr Thr Thr Arg Val Gln His Ala Ser Pro Ala
                165                 170                 175
Gly Ala Tyr Ala His Thr Val Asn Arg Asn Trp Tyr Ser Asp Ala Asp
            180                 185                 190
Val Pro Ala Ser Ala Arg Gln Glu Gly Cys Gln Asp Ile Ala Thr Gln
            195                 200                 205
Leu Ile Ser Asn Met Asp Ile Asp Val Ile Leu Gly Gly Gly Arg Lys
210                 215                 220
Tyr Met Phe Pro Met Gly Thr Pro Asp Pro Glu Tyr Pro Asp Asp Tyr
225                 230                 235                 240
Ser Gln Gly Gly Thr Arg Leu Asp Gly Lys Asn Leu Val Gln Glu Trp
                245                 250                 255
Leu Ala Lys His Gln Gly Ala Arg Tyr Val Trp Asn Arg Thr Glu Leu
            260                 265                 270
Leu Gln Ala Ser Leu Asp Pro Ser Val Thr His Leu Met Gly Leu Phe
            275                 280                 285
Glu Pro Gly Asp Met Lys Tyr Glu Ile His Arg Asp Ser Thr Leu Asp
            290                 295                 300
Pro Ser Leu Met Glu Met Thr Glu Ala Ala Leu Leu Leu Leu Ser Arg
305                 310                 315                 320
Asn Pro Arg Gly Phe Phe Leu Phe Val Glu Gly Gly Arg Ile Asp His
                325                 330                 335
Gly His His Glu Ser Arg Ala Tyr Arg Ala Leu Thr Glu Thr Ile Met
            340                 345                 350
Phe Asp Asp Ala Ile Glu Arg Ala Gly Gln Leu Thr Ser Glu Glu Asp
            355                 360                 365
Thr Leu Ser Leu Val Thr Ala Asp His Ser His Val Phe Ser Phe Gly
370                 375                 380
Gly Tyr Pro Leu Arg Gly Ser Ser Ile Phe Gly Leu Ala Pro Gly Lys
385                 390                 395                 400
Ala Arg Asp Arg Lys Ala Tyr Thr Val Leu Leu Tyr Gly Asn Gly Pro
                405                 410                 415
Gly Tyr Val Leu Lys Asp Gly Ala Arg Pro Asp Val Thr Glu Ser Glu
            420                 425                 430
Ser Gly Ser Pro Glu Tyr Arg Gln Gln Ser Ala Val Pro Leu Asp Gly
            435                 440                 445
Glu Thr His Ala Gly Glu Asp Val Ala Val Phe Ala Arg Gly Pro Gln
450                 455                 460
Ala His Leu Val His Gly Val Gln Glu Gln Thr Phe Ile Ala His Val
465                 470                 475                 480
Met Ala Phe Ala Ala Cys Leu Glu Pro Tyr Thr Ala Cys Asp Leu Ala
                485                 490                 495
Pro Arg Ala Gly Thr Thr Asp Ala Ala His Pro Gly Pro Ser Val Val
            500                 505                 510
Pro Ala Leu Leu Pro Leu Leu Ala Gly Thr Leu Leu Leu Leu Gly Thr
            515                 520                 525
Ala Thr Ala Pro
```

<210> SEQ ID NO 19
<211> LENGTH: 528
<212> TYPE: PRT
<213> ORGANISM: Homo sapiens

<400> SEQUENCE: 19

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
50                      55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

```
Thr Leu Thr Leu Val Thr Ala Asp His Ser His Val Phe Ser Phe Gly
        370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Ala Ala Val Pro Leu Ser Ser
                435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
                515                 520                 525
```

<210> SEQ ID NO 20
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
    195                 200                 205
```

```
His Glu Ala Leu His Asn His Tyr Thr Gln Lys Ser Leu Ser Leu Ser
    210                 215                 220
Pro Gly Lys
225
```